US009427306B2

(12) United States Patent
Shahriari

(10) Patent No.: US 9,427,306 B2
(45) Date of Patent: Aug. 30, 2016

(54) VARIABLE DEPRESSION STENTS (VDS) AND BILLOWING GRAFT ASSEMBLIES

(71) Applicant: Aortic Innovations Surena, LLC, Boca Raton, FL (US)

(72) Inventor: Ali Shahriari, Boca Raton, FL (US)

(73) Assignee: Aortic Innovations Surena, LLC, Boca Raton, FL (US)

( * ) Notice: Subject to any disclaimer, the term of this patent is extended or adjusted under 35 U.S.C. 154(b) by 0 days.

(21) Appl. No.: 14/551,103

(22) Filed: Nov. 24, 2014

(65) Prior Publication Data

US 2015/0105850 A1    Apr. 16, 2015

Related U.S. Application Data

(63) Continuation of application No. PCT/US2014/041185, filed on Jun. 5, 2014.

(60) Provisional application No. 62/001,916, filed on May 22, 2014, provisional application No. 61/940,866,
(Continued)

(51) Int. Cl.
*A61F 2/07* (2013.01)
*A61F 2/856* (2013.01)
(Continued)

(52) U.S. Cl.
CPC .................. *A61F 2/07* (2013.01); *A61F 2/856* (2013.01); *A61F 2/90* (2013.01); *A61F 2/89* (2013.01);
(Continued)

(58) Field of Classification Search
CPC ...... A61F 2002/072; A61F 2/82; A61F 2/07; A61F 2002/826; A61F 2002/828; A61F 2/852; A61F 2/856; A61F 2/86; A61F 2/89; A61F 2/90; A61F 2/915–2002/9155; A61F 2002/821; A61F 2250/0039; A61F 2/954; A61F 2002/075
USPC ........................................................ 623/1.29
See application file for complete search history.

(56) References Cited

U.S. PATENT DOCUMENTS 5,395,390 A    3/1995  Simon et al.
5,716,393 A    2/1998  Lindenberg et al.
(Continued)

FOREIGN PATENT DOCUMENTS

CA          2501892 A1    12/1999
WO       2009056644 A1     7/2009
WO       2012147675 A1    11/2012

OTHER PUBLICATIONS

ISR dated Oct. 28, 2014 for International Application PCT/2014/041185.
(Continued)

*Primary Examiner* — Christopher D Prone
(74) *Attorney, Agent, or Firm* — NK Patent Law, PLLC

(57) ABSTRACT

A stent assembly includes support rings each having interconnected circumferentially alternating inner prongs and outer prongs. The inner prongs define an inner diameter around a longitudinal axis. The outer prongs define an outer diameter greater than the inner diameter. A graft engages the support rings and follows a waving peripheral path. The graft may be a billowing graft. A second graft may surround the first graft such that tunnels are defined between the first graft and second graft. A method of making a stent assembly includes diametrically expanding the support rings onto a mandrel, engaging a graft with the support rings, and removing the support rings and graft from the mandrel permitting the stent assembly to contract to a neutral state.

28 Claims, 28 Drawing Sheets

Related U.S. Application Data filed on Feb. 18, 2014, provisional application No. 61/940,865, filed on Feb. 18, 2014, provisional application No. 61/940,327, filed on Feb. 14, 2014, provisional application No. 61/879,928, filed on Sep. 19, 2013, provisional application No. 61/863,745, filed on Aug. 8, 2013, provisional application No. 61/831,196, filed on Jun. 5, 2013.

(51) Int. Cl.
*A61F 2/90* (2013.01)
*A61F 2/89* (2013.01)
*A61F 2/06* (2013.01)

(52) U.S. Cl.
CPC .... *A61F 2002/061* (2013.01); *A61F 2002/067* (2013.01); *A61F 2002/075* (2013.01); *A61F 2230/0008* (2013.01); *A61F 2230/0034* (2013.01); *A61F 2230/0054* (2013.01); *A61F 2230/0067* (2013.01); *A61F 2240/001* (2013.01); *A61F 2250/0039* (2013.01); *A61F 2250/0098* (2013.01); *Y10T 29/49863* (2015.01)

(56) References Cited

U.S. PATENT DOCUMENTS

| | | | |
|---|---|---|---|
| 6,162,245 A * | 12/2000 | Jayaraman | A61F 2/07 623/1.15 |
| 6,174,328 B1 | 1/2001 | Cragg | |
| 6,254,632 B1 | 7/2001 | Wu et al. | |
| 6,334,868 B1 | 1/2002 | Ham | |
| 6,645,242 B1 | 11/2003 | Quinn | |
| 6,752,829 B2 | 6/2004 | Kocur et al. | |
| 6,776,793 B2 | 8/2004 | Brown et al. | |
| 7,122,052 B2 | 10/2006 | Greenhalgh | |
| 8,172,895 B2 | 5/2012 | Anderson | |
| 8,348,988 B2 | 1/2013 | Lad et al. | |
| 8,425,584 B2 | 4/2013 | Cully et al. | |
| 2003/0040771 A1 | 2/2003 | Hyodoh et al. | |
| 2005/0197687 A1 | 9/2005 | Molaei et al. | |
| 2006/0149351 A1 | 7/2006 | Smirthwaite et al. | |
| 2007/0156229 A1 * | 7/2007 | Park | A61F 2/07 623/1.15 |
| 2007/0250146 A1 | 10/2007 | Cully et al. | |
| 2007/0276464 A1 | 11/2007 | Valencia et al. | |
| 2008/0132999 A1 | 6/2008 | Mericle et al. | |
| 2008/0312732 A1 * | 12/2008 | Hartley | A61F 2/07 623/1.13 |
| 2009/0082846 A1 * | 3/2009 | Chobotov | 623/1.13 |
| 2009/0099644 A1 | 4/2009 | Biadillah et al. | |
| 2009/0171442 A1 | 7/2009 | Young et al. | |
| 2009/0198315 A1 | 8/2009 | Boudjemline | |
| 2010/0042202 A1 | 2/2010 | Ramzipoor et al. | |
| 2012/0123524 A1 | 5/2012 | Girton et al. | |
| 2013/0116773 A1 | 5/2013 | Roeder et al. | |

OTHER PUBLICATIONS

Singh, "A biomimetic approach for designing stent-graft structures: Caterpillar cuticle as design model," Journal of the Mechanical Behavior of Biomedical Materials, Feb. 2014, No. 30, pp. 16-29.
Kelly, "Complication During Complete Endovascular Repair of a Thoracic Aortic Aneurysm," MD FACS, 2014, 26 pages.
Search Report mailed May 1, 2015 for international application No. PCT/US2015/015959.
WIPO, International Preliminary Report on Patentability for PCT Patent Application PCT/US2014/041185, Dec. 8, 2015.

* cited by examiner

VARIABLE DEPRESSION STENTS (VDS) AND BILLOWING GRAFT ASSEMBLIES

CROSS-REFERENCE TO RELATED APPLICATION

This application is a continuation of PCT Application No. PCT/US14/41185 filed on Jun. 5, 2014, titled "Variable Depression Stents (VDS) and Billowing Graft Assemblies" which claims the benefit of priority of each of U.S. provisional patent applications: 61/831,196, titled "Suprarenal Endograft and Method," filed on Jun. 5, 2013; 61/863,745, titled "Variable Depression Stent with Billowing Graft," filed on Aug. 8, 2013; 61/879,928, titled "Suprarenal Endograft with Variable Depression Stent," filed on Sep. 19, 2013; 61/940,866, titled "Endograft Adaptable for use in Multiple Locations of Abdominal Aorta," filed on Feb. 18, 2014; 61/940,865, titled "Suprarenal Endograft with Variable Depression Stent," filed on Feb. 18, 2014; 62/001,916 filed on May 22, 2014; and 61/940,327 filed on Feb. 14, 2014, titled "Branched Aortic Graft and Method of Using the Same", all of which are incorporated herein in entirety by this reference.

TECHNICAL FIELD

The present disclosure relates to devices that may be used to treat aortic aneurysms. The devices described may also be used for the treatment of thoracoabdominal, arch and ascending aneurysms.

BACKGROUND

Endovascular technology has revolutionized the treatment of abdominal aortic aneurysms. This technology has shifted the treatment of these deadly disorders from an invasive, morbid operation to a minimally invasive option with low morbidity and mortality and length of stay. Although many patients are candidates for this less invasive repair with conventional devices, a large group of patients are not treatable because of anatomical restrictions. Some of these patients may be candidates for treatment with conventional fenestrated endografts, however there are significant limitations to the use of that technology. These limitations are often secondary to poor iliofemoral access (because of the large profile of the current devices), angulations in the aorta, the degree of angulation and disease within the renal arteries, technical limitations with regard to the creation of the holes in the current endografts or a combination thereof. Another limitation to the current available technology is the fact that a device may need to be created for each individual patient, adding delays of between three to six weeks to the treatment of the patients and patients with urgent/emergent needs would be ineligible for this treatment.

SUMMARY

This summary is provided to introduce in a simplified form concepts that are further described in the following detailed descriptions. This Summary is not intended to identify key features or essential features of the claimed subject matter, nor is it to be construed as limiting the scope of the claimed subject matter.

A stent assembly according to at least one embodiment includes a first support ring, a second support ring, and a billowing graft. Each support ring may be made of shape memory wire, stainless steel, or other materials. The first support ring has interconnected circumferentially alternating first inner prongs and first outer prongs, the first inner prongs defining a first inner diameter around a central longitudinal axis, and the first outer prongs defining a first outer diameter around the central longitudinal axis greater than the first inner diameter. The second support ring is spaced from the first support ring along the central longitudinal axis. The second support ring has interconnected circumferentially alternating second inner prongs and second outer prongs, the second inner prongs defining a second inner diameter around the central longitudinal axis, and the second outer prongs defining a second outer diameter around the central longitudinal axis greater than the second inner diameter. The billowing graft engages the first support ring and second support ring, the billowing graft following a waving peripheral path at least partially around at least one of the first support ring and second support ring.

In at least one example, a circumferential position of a particular first inner prong is aligned with a circumferential position of a particular second inner prong, and circumferential positions of two first outer prongs adjacent the particular first inner prong are aligned respectively with circumferential positions of two second outer prongs adjacent the particular second inner prong such that a longitudinal channel is defined along the aligned circumferential positions of the particular first inner prong and particular second inner prong.

In at least one example, the billowing graft billows along the longitudinal channel.

In at least one example, the billowing graft is attached to the two first outer prongs adjacent the particular first inner prong and to the two second outer prongs adjacent the particular second inner prong.

In at least one example, the billowing graft is free to billow radially outward from and radially inward toward the particular first inner prong and the particular first inner prong along the longitudinal channel.

In at least one example, at least one side stent is positioned at least partially within the longitudinal channel.

In at least one example, the first inner prongs have tips directed in a first longitudinal direction; and the first outer prongs have tips directed in a second longitudinal direction opposite the first longitudinal direction.

In at least one example, the first support ring further has a radially flat portion defined by at least two prongs that extend in opposite longitudinal directions, the at least two prongs of the radially flat portion of the first support ring being equidistant from the central longitudinal axis.

In at least one example, the first outer prongs and the at least two prongs of the radially flat portion of the first support ring are equidistant from the central longitudinal axis.

In at least one example, the second support ring further has a radially flat portion defined by at least two prongs that extend in opposite longitudinal directions, the at least two prongs of the radially flat portion of the second support ring being equidistant from the central longitudinal axis.

In at least one example, the radially flat portion of the first support ring has a circumferential position aligned with a circumferential position of the radially flat portion of the second support ring.

In at least one example, an angle subtended partially around the central longitudinal axis by the radially flat portion of the first support ring is approximately equal to an angle subtended partially around the central longitudinal axis by the radially flat portion of the second support ring.

In at least one example, the angle subtended partially around the central longitudinal axis by the radially flat portion of the first support ring is less than one hundred and eighty degrees.

In at least one example, the first inner prongs and first outer prongs are connected together by intermediate connecting segments; and the first inner prongs, first outer prongs and intermediate connecting segments together subtend a summation angle of greater than one hundred and eighty degrees around the central longitudinal axis.

In at least one example, the first support ring comprises a first portion including the first inner prongs and first outer prongs and a second portion including the radially flat portion of the first support ring; and the first portion of the first support ring is C-shaped and subtends an angle of greater than one hundred and eighty degrees around the central longitudinal axis.

In at least one example, the second inner prongs have tips directed in the first longitudinal direction; and the second outer prongs have tips directed in the second longitudinal direction opposite the first longitudinal direction.

In at least one example, the second outer prongs have tips directed in the first longitudinal direction; and the second inner prongs have tips directed in the second longitudinal direction opposite the first longitudinal direction.

In at least one example, at least one fenestration for receiving a vessel is formed through the billowing graft.

In at least one example, a radio-opaque marker is placed around the at least one fenestration.

In at least one example, the fenestration is formed through the billowing graft at a circumferential position corresponding to a circumferential position of a radially flat portion of the first support ring and a circumferential position of a radially flat portion of the second support ring.

In at least one embodiment, a method for forming a stent assembly includes: providing a first support ring having interconnected circumferentially alternating first inner prongs and first outer prongs, the first support ring having a neutral state in which the first inner prongs define a first inner diameter around a central longitudinal axis, and in which the first outer prongs define a first outer diameter around the central longitudinal axis greater than the first inner diameter; providing a mandrel having at least one portion with a diameter greater than the first outer diameter; diametrically expanding the first support ring from the neutral state and at least partially surrounding the at least one portion of the mandrel with the first outer prongs; at least partially surrounding the first outer prongs with a graft; engaging the graft with the first outer prongs; removing the first support ring and graft from the mandrel; and permitting the first support ring to diametrically contract to the neutral state such that the graft follows a waving peripheral path at least partially around the first support ring.

In at least one example, the at least one portion of the mandrel with a diameter greater than the first outer diameter is a first longitudinal portion of the mandrel having a first mandrel diameter greater than the first outer diameter. The mandrel further has a second longitudinal portion adjacent the first longitudinal portion of the mandrel. The second longitudinal portion of the mandrel has a second mandrel diameter that is less than the first mandrel diameter and greater than the first inner diameter. The method further comprises at least partially surrounding the second longitudinal portion of the mandrel with the first inner prongs.

In at least one example, the graft has an exterior side and an interior side and the graft has pockets defined along the interior side. Engaging the graft with the first outer prongs includes inserting the first outer prongs into the pockets.

In at least one embodiment, a stent assembly includes a first support ring, a second support ring, a first graft, and a second graft. The first support ring has interconnected circumferentially alternating first inner portions and first outer portions, the first inner portions defining a first inner diameter around a central longitudinal axis, and the first outer portions defining a first outer diameter around the central longitudinal axis greater than the first inner diameter.

The second support ring is spaced from the first support ring along the central longitudinal axis. The second support ring has interconnected circumferentially alternating second inner portions and second outer portions, the second inner portions defining a second inner diameter around the central longitudinal axis, and the second outer portions defining a second outer diameter around the central longitudinal axis greater than the second inner diameter. The first graft engages the first support ring and second support ring, the first graft following a waving peripheral path at least partially around each of the first support ring and second support ring. The second graft at least partially surrounds the first graft such that longitudinal tunnels are defined between first graft and second graft. The second graft may be supported by a wire skeleton or stents.

In at least one example: the first inner portions of the first support ring have circumferential positions aligned with circumferential positions of the second inner portions of the second support ring; the first outer portions of the first support ring have circumferential positions aligned with circumferential positions of the second outer portions of the second support ring; the first graft has radially depressed channels extending longitudinally at the circumferential positions of the first inner portions of the first support ring; and the longitudinal tunnels are defined between the radially depressed channels and the second graft.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

DETAILED DESCRIPTIONS

Figure 1:
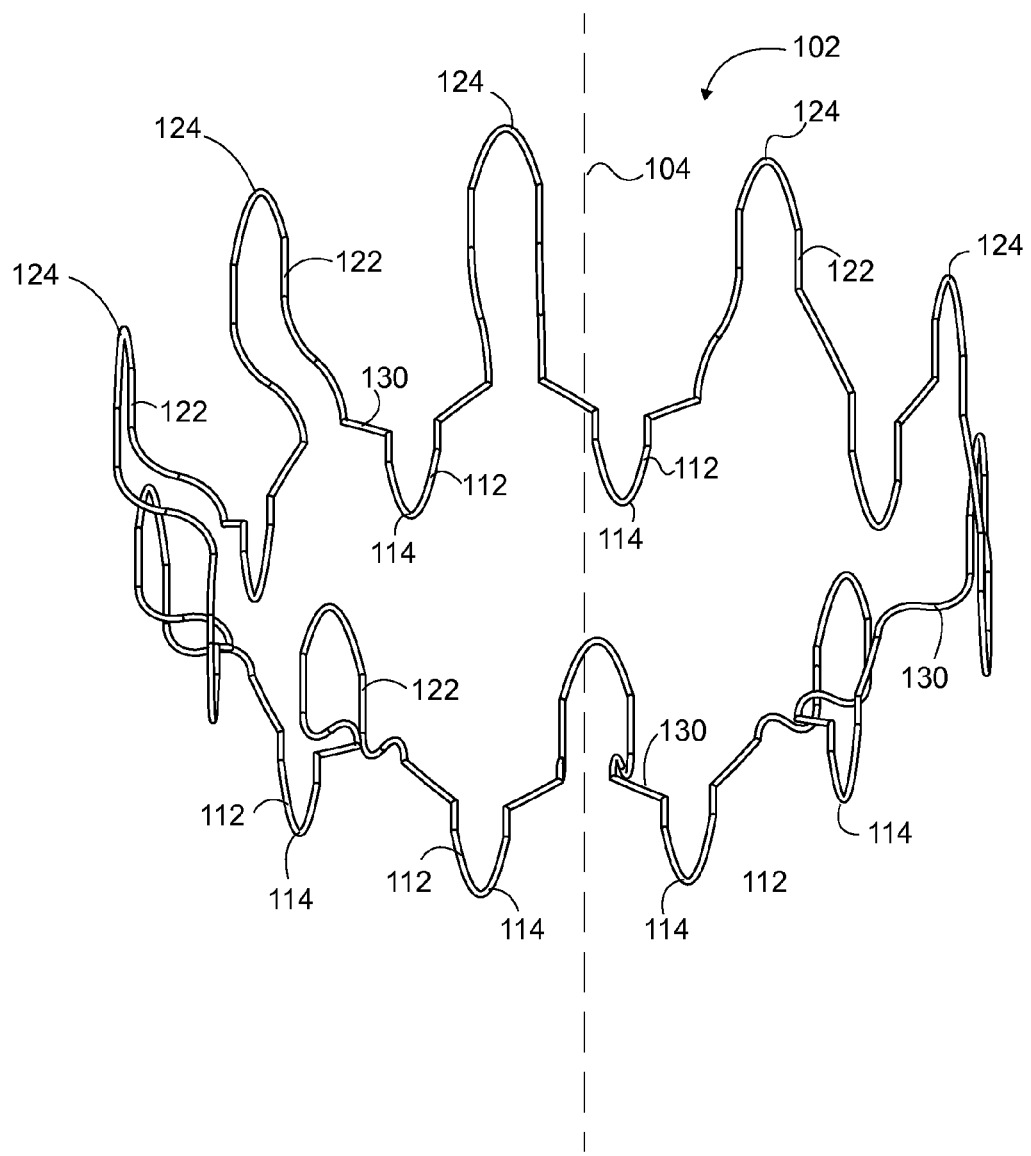
FIG. 1 is a perspective view of a support ring according to at least one embodiment.

These descriptions are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

Terms representing anatomical references, such as anterior, posterior, medial, lateral, superior, inferior, caudal, cranial, etcetera, may be used throughout the specification in reference to the implants and surgical instruments described herein as well as in reference to the patient's natural anatomy. Such terms have well-understood meanings in both the study of anatomy. Use of such anatomical reference terms in the written description and claims is intended to be consistent with their well-understood meanings unless noted otherwise. For example, the term "cranial" refers to the direction that is generally toward the head of the patient, and the term "caudal" refers to the direction that is generally toward the feet of the patient.

The design and geometrical shape of the endograft stent assemblies detailed in these descriptions permit separate access to the renal arteries, thus facilitating use with many anatomical variations. These designs allow for placement of parallel covered renal stents while reducing the likelihood of an endoleak along the renal stents, and reducing the risk of kinking and compression of the renal stents.

Figure 2:
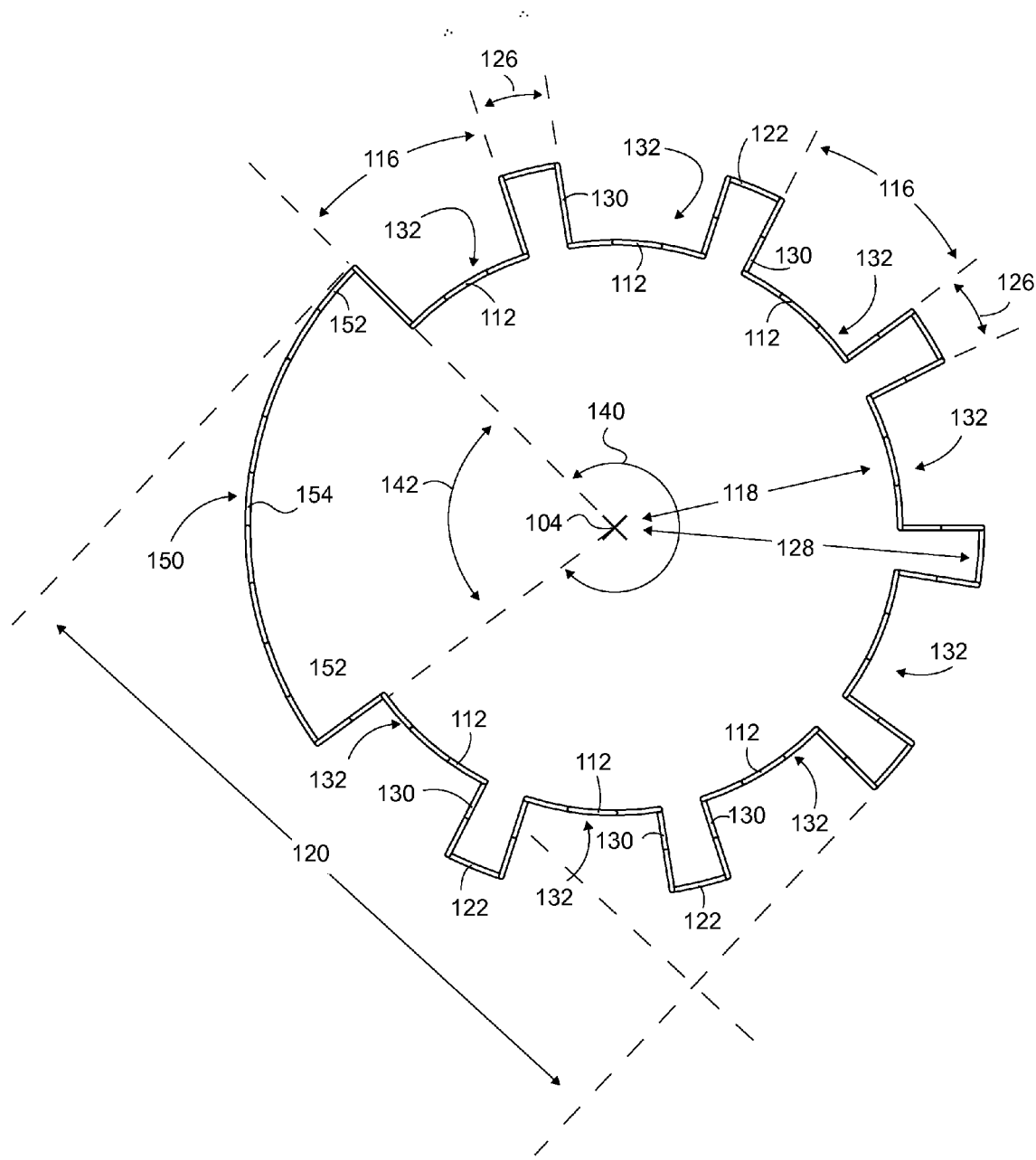
FIG. 2 is a plan view of the support ring of FIG. 1.
Figure 3:
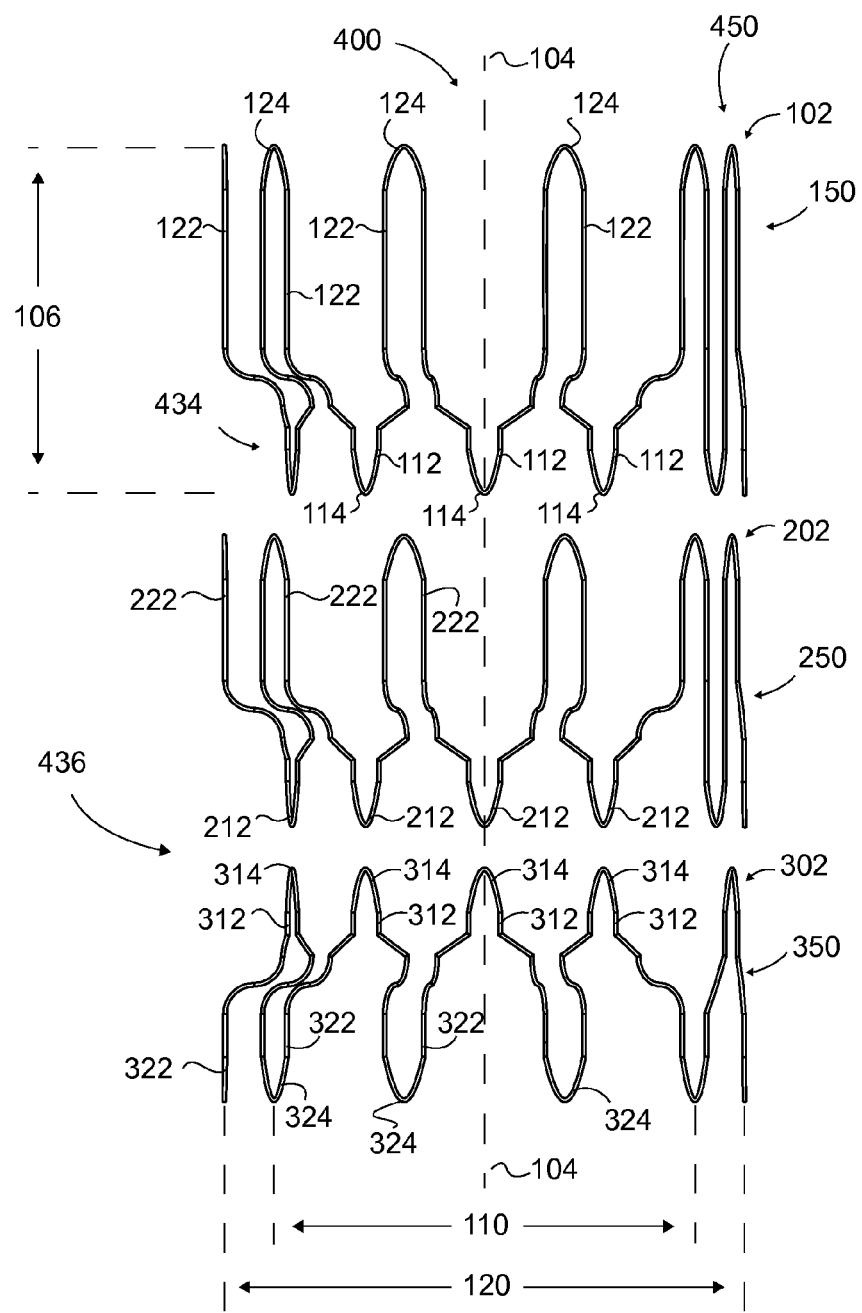
FIG. 3 is an elevation view of a variable depression stent (VDS) frame including three support rings according to at least one embodiment.

An embodiment of a support ring 102 is shown in FIGS. 1 and 2. The support ring 102 has two distinct diameters, namely an inner diameter 110 and a greater outer diameter 120, defined respectively by alternating inner prongs 112 and outer prongs 122 of the support ring. The inner prongs 112 are connected to the outer prongs 122 by intermediate connecting segments 130. The support ring surrounds a longitudinal axis 104, and defines a longitudinal length 106 between oppositely directed tips 114 of the inner prongs 112 and tips 124 of the outer prongs 122. In at least one embodiment, the support ring 102 is formed from one continuous wire. These descriptions nonetheless refer to segments of the support ring 112 as prongs, tips, and connecting segments for the purpose of detailing the support ring. In FIGS. 1 and 3, the tips 114 of the inner prongs 112 are shown as downwardly directed and the tips 124 of the outer prongs 122 are shown upwardly directed. This particular orientation is depicted for exemplary purposes. Other orientations may be preferred and are within the scope of these descriptions and the drawings.

For example, FIG. 3 illustrates a stent frame 400 including three support rings, each generally within the scope of the descriptions of the support ring 102. In particular, the stent frame 400 includes same-oriented upper and middle support rings 102 and 202, and one oppositely oriented lower support ring 302. More particularly, the lower support ring 302 is illustrated as having its inner prong tips 314 upwardly directed and its outer prong tips 324 downwardly directed. Thus, FIG. 3 depicts one example of multiple support rings together forming a stent frame 400 having an inner diameter 110 and a greater outer diameter 120.

FIG. 3 illustrates the support rings 102, 202 and 302 as approximately concentric with the longitudinal axis and spaced along the longitudinal axis 104 without expressly illustrating any interconnecting structure among the support rings. As further detailed in the following descriptions, the support rings in at least one embodiment are interconnected and maintained in their relative positions by a cover, for example the major cover graft 502 that generally surrounds the stent frame 400 in FIGS. 5 and 6.

Figure 4:
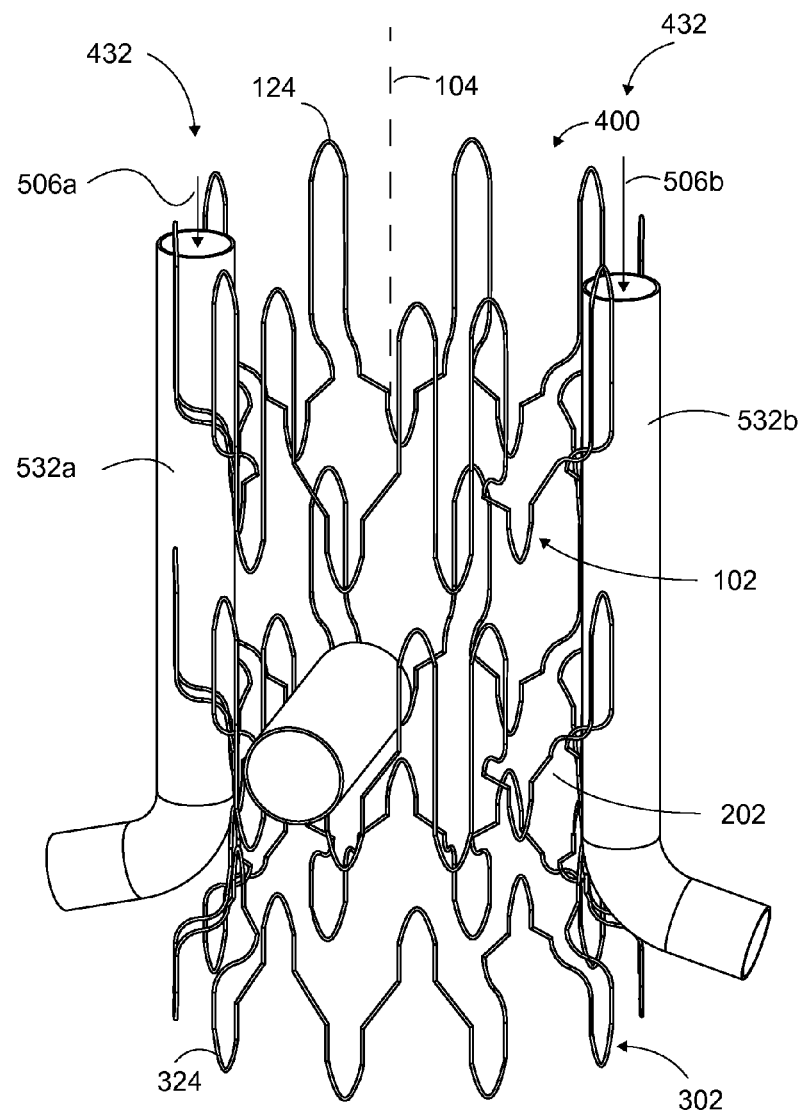
FIG. 4 is a perspective view of the support frame of FIG. 3 with several arterial stents supported by longitudinal grooves.
Figure 5:
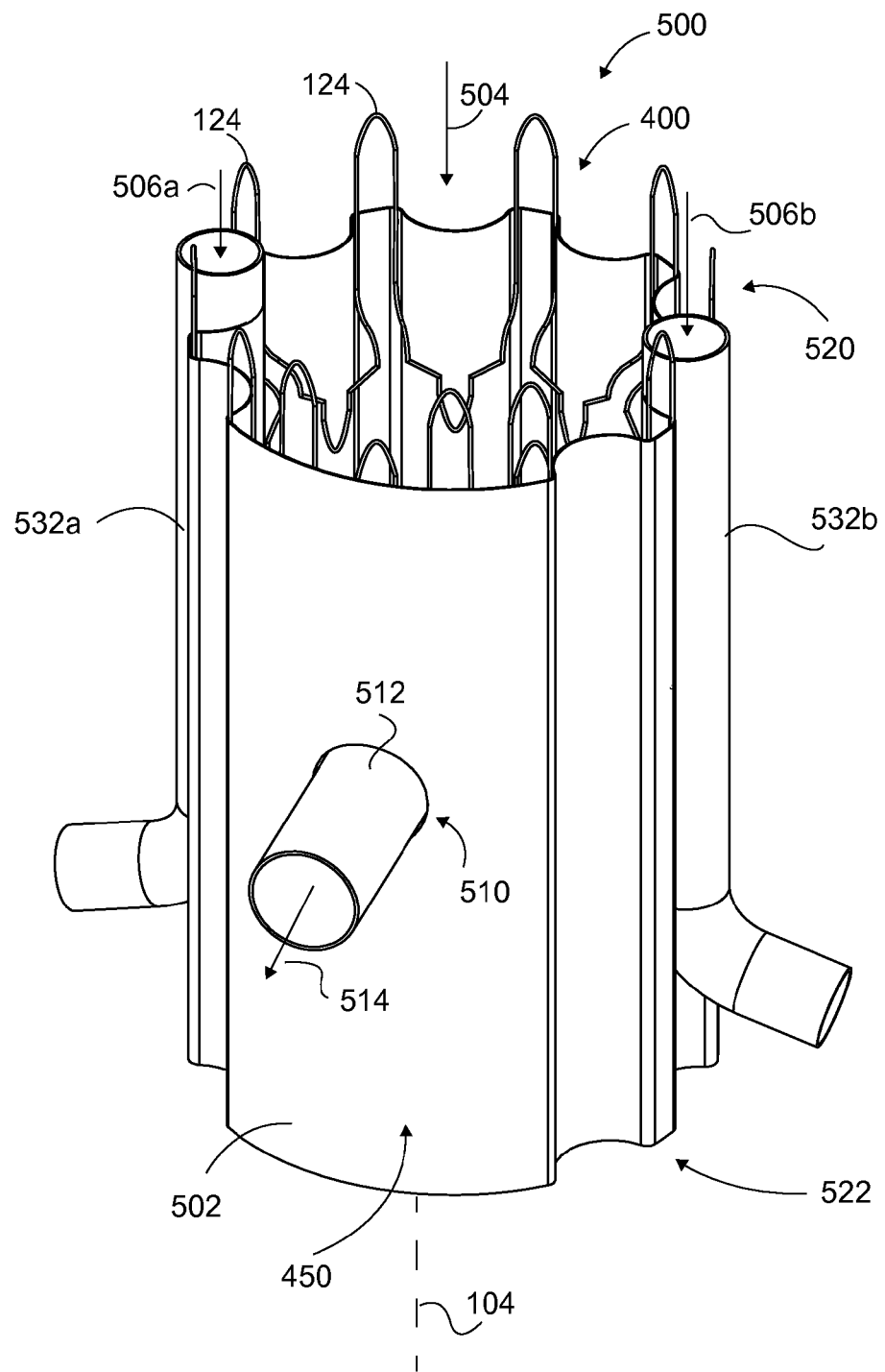
FIG. 5 is a perspective view of a VDS stent assembly including a billowing graft and several arterial stents supported by longitudinal grooves according to at least one embodiment.

With brief reference now to FIGS. 4 and 5 to appreciate advantages of the stent frame 400, a first longitudinal side stent 532a and a second longitudinal side stent 532b are shown in FIG. 4 as cradled within exterior longitudinal channels defined by the stent frame 400. In such cradled engagement with the stent frame 400, the side stents 532a and 532b are supported by the support rings in use when blood pressure is applied. FIG. 5 includes also a major cover graft 502 generally surrounding the stent frame 400, between the stent frame 400 and the side stents 532a and 532b. A central fluid flow channel 504 is defined within the major cover graft 502 along the longitudinal axis 104. Longitudinal grooves for the side stents 532a and 532b are formed where the graft material is in contact with the side stents. Longitudinal fluid flow channels 506a and 506b are defined respectively within the side stents 532a and 532b. In other embodiments, additional parallel side stents can be included. In the stent assembly 500 of FIG. 5, blood pressure can bear upon the major cover graft 502 from within, and arterial or aortic tissue can be contacted along the exterior of the stent assembly 500, while the side stents 532a and 532b are supported and localized within the longitudinal grooves formed between the cover graft 502 and tissue by the support rings 102, 202 and 302 of the stent frame 400.

Returning to FIGS. 1 and 2 to further describe each support ring, the inner prongs 112 and outer prongs 122 each subtend a circumferential angle as shown in FIG. 2. Each inner prong 112 is illustrated as subtending a greater circumferential angle 116 than the circumferential angle 126 subtended by each outer prong 122. Other proportions than that expressly depicted in FIG. 2 are within the scope of these descriptions. As shown best in FIG. 2, the circumferential angles 116 and 126 subtended by the inner prongs 112 and outer prongs 122 sum to a circumferential summation angle 140 that is less than three hundred and sixty (360) degrees such that the longitudinal axis is only partially circumferentially surrounded by the inner prongs 112 and outer prongs 122 connected by the intermediate connecting segments 130.

The support ring 102 further includes a radially flat portion 150, illustrated as having two commonly directed prongs 152 at the circumferential margins of the flat portion 150 and an oppositely directed central prong 154. The radially flat portion 150 is distinct from other portions of the support ring 100 in that it lies in a cylindrical surface equidistant from the central longitudinal axis 104, whereas the inner prongs 112 and outer prongs 122 lie at alternating respective near and far radial distances 118 and 128 from the axis 104 with the intermediate connecting segments 130 spanning the radial difference between the near and far radial distances 118 and 128, which measure as halves of the inner and outer diameters 110 and 120 respectively. Thus, the support ring has a first circumferential portion subtending a first angle 140 and defined by alternating radially inner and outer prongs 112 and 114 with respect to the longitudinal axis 104, and a second circumferential portion subtending a second angle 142 and defined by a radially flat portion 150 at a uniform distance from the central longitudinal axis 104, that uniform distance being the far radial distance 128. The sum of the subtended first angle 140 and the subtended second angle 142 is equal to three hundred and sixty (360) degrees. In the illustrated embodiment, the first portion is C-shaped as defined by the summation angle 140 being greater than one hundred and eighty (180) degrees.

As shown in FIGS. 1 and 3, each inner prong 112 is defined by a U-shaped element having two linear longitudinally extending portions connected by the tip 114. Similarly, each outer prong 122 is defined by a U-shaped element having two linear longitudinally extending portions connected by the tip 124. The connecting segments 130 are curvilinear, extending both longitudinally and radially. For example, when viewed along a side as shown in FIG. 3, from a view perpendicular to the longitudinal axis, the connecting segments 130 appear as S-shaped.

In the stent frame 400 of FIG. 3, the inner prongs 112 of the support ring 102, the inner prongs 212 of the support ring 202, and the inner prongs 312 of the support ring 302 are aligned with regard to their circumferential positions. Similarly, the outer prongs 122 of the support ring 102, the outer prongs 222 of the support ring 202, and the outer prongs 322 of the support ring 302, are aligned. Thus, the radial depressions 132 (FIG. 2), which are defined radially outward from the inner prongs 112 and circumferentially between the connecting segments 130 at either side of each inner prong 112 of support ring 102, align with depressions similarly defined by corresponding portions of the support ring 202. The depressions 132 are also aligned with depressions similarly defined by corresponding portions of the support ring 302. As such, exterior longitudinal channels 432 are defined by the stent frame 400 to cradle the first longitudinal arterial stent 532a and second longitudinal arterial stent 532b as shown in FIG. 4. Additional longitudinal side stents may be similarly cradled in the unfilled exterior longitudinal channels. Thus, these descriptions refer to the variable depression stent (VDS) frame 300 with respect to FIG. 3. With regard to the assembly shown in FIG. 5, which includes the VDS frame 300, the first longitudinal side stent 532a, the second longitudinal side stent 532b, and the major cover graft 502, these description refer to a variable depression stent (VDS) assembly 500.

In the stacked arrangement of support rings 102, 202 and 302 in the stent frame 400 of FIG. 3, circumferential channels partially surround the longitudinal axis 104. In particular, a first circumferential channel 434 is defined radially outward from the inner prongs 112 of the support ring 102 longitudinally between the outer prongs 122 of the support ring 102 and the outer prongs 222 of the support ring 202. Similarly, a second circumferential channel 436 is defined radially outward from the inner prongs 212 of the support ring 202 and inner prongs 312 of the support ring 302 longitudinally between the outer prongs 222 of the support ring 202 and the outer prongs 322 of the support ring 302. Thus the stent frame 400 has the inner diameter 110 along the circumferential channels 434 and 436, corresponding to the inner diameter 110 of the support rings 102, 202, 302 in those circumferential portions corresponding to the circumferential summation angle 140 (FIG. 2). The stent frame 400 has the outer diameter 120 elsewhere, including full circular peripheries at the longitudinal positions of the outer prongs 122, 222 and 322, and partial circular peripheries subtending the angle 142 (FIG. 2) corresponding to the longitudinal and circumferential positions of the radially flat portions 150, 250 and 350 of the support rings. Thus, the stent frame 400 has a radially flat portion 450 corresponding to the circumferential locations of radially flat portions 150, 250 and 350 of the support rings.

Figure 6:
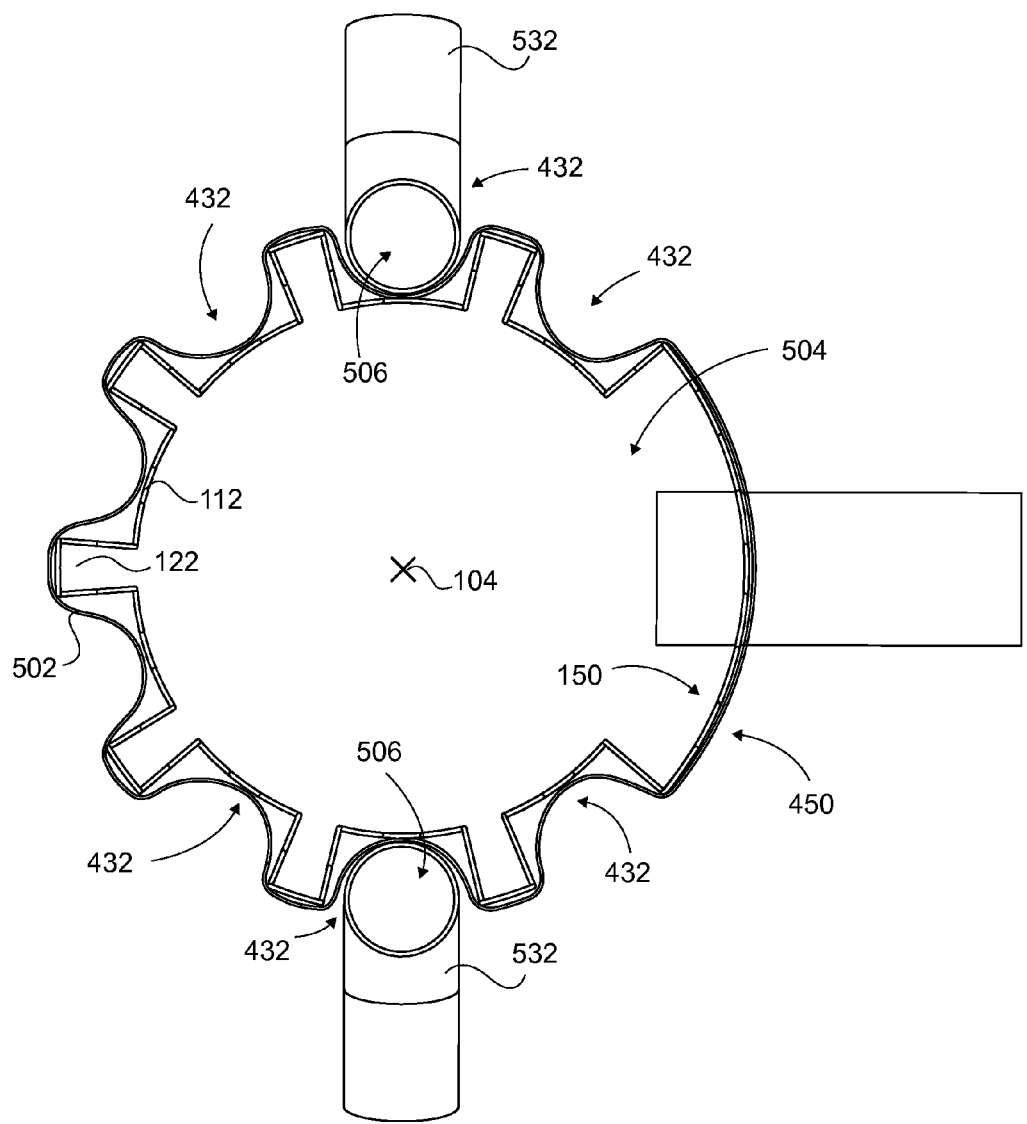
FIG. 6 is a longitudinal end plan view of the VDS stent assembly of FIG. 5.

The VDS assembly 500 is shown in FIG. 6 along the longitudinal axis as viewed from above the upper longitudinal end 520 of the assembly in FIG. 5. A billowing aspect of the major cover graft 502 can be understood from viewing FIG. 6. In the illustrated neutral state of the major cover graft 502 as shown in FIG. 6, a waving state of the graft 502 is seen due to the major cover graft 502 following a waving peripheral path around the stent frame 400. The path length of the waving peripheral path of the major cover graft 502 is greater than an outer circumference of the stent frame 400 as prescribed by the outer diameter 120 defined by the outer prongs 122, 222 and 322 of the support rings 100, 200 and 300. As such, when the stent frame 400 is in its diametrically neutral state as shown in FIG. 6, excess material of the graft 502 billows.

In particular, portions of the graft 502 overlying the circumferential positions of the exterior longitudinal channels 432 defined by the stent frame 400 are shown as billowed inward in FIG. 6. Portions of the graft 502 overlying the circumferential positions of the outer prongs 122, 222 and 322 (see also FIG. 3), are maintained radially outward from the longitudinal channels 432.

In use in which, for example, blood flows along central fluid flow channel 504 toward the lower longitudinal end 522 of the VDS assembly 500, the graft 502 is expected to billow outwardly to contact arterial or aortic tissue along the exterior of the graft 502. The side stents 532a and 532b are supported and localized within the longitudinal channels 432 between the major cover graft 502 and the tissue. This facilitates blood flow within the longitudinal fluid flow channels 506a and 506b defined within the side stents 532a and 532b. The billowing properties of the graft will create a complete seal along the side stents 532a and 532b. As such, these descriptions refer to the VDS assembly 500 as having a billowing graft, referring to the billowing aspect of the major cover graft 502.

Figure 7:
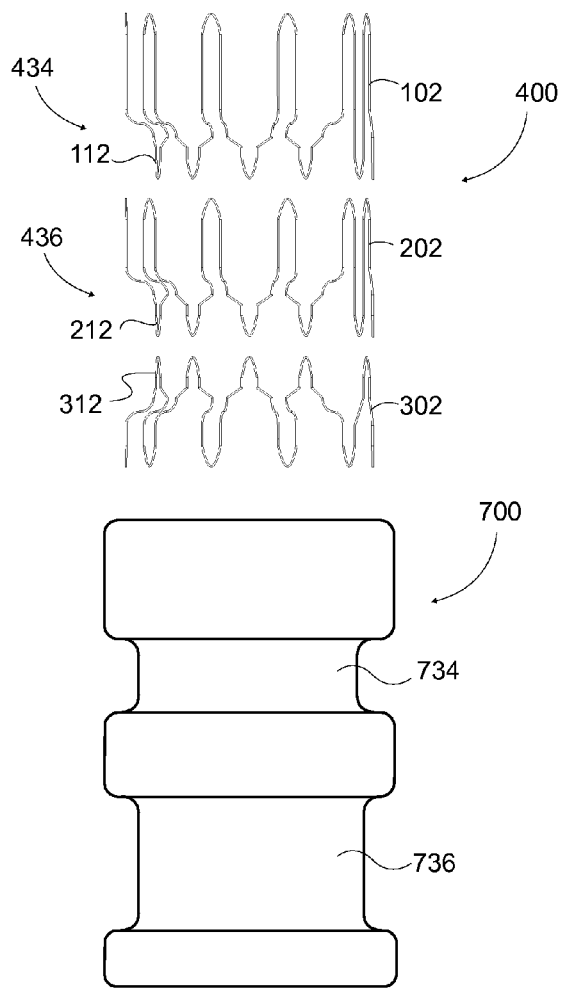
FIG. 7 is an elevation view of the VDS frame of FIG. 3 and a mandrel according to at least one embodiment.
Figure 8:
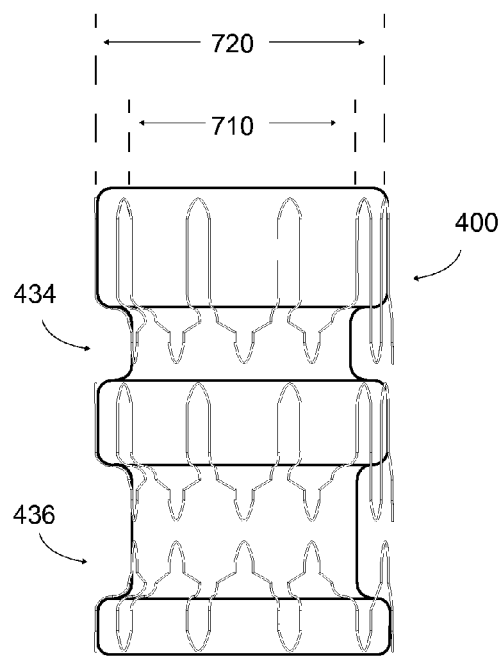
FIG. 8 is an elevation view of the VDS frame of FIG. 3 diametrically stretched onto the mandrel of FIG. 7 in preparation for engagement with the graft of FIG. 5.
Figure 9:
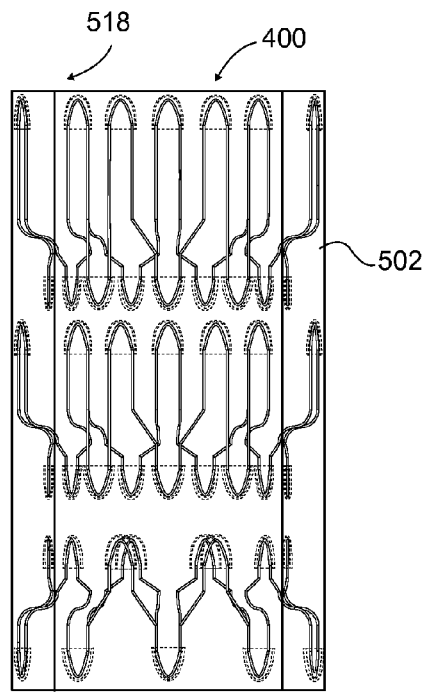
FIG. 9 is an elevation view of the VDS frame of FIG. 3 engaged with the graft of FIG. 5 by pockets according to at least one embodiment.

Assembly of the billowing graft VDS assembly 500, and other billowing graft VDS assemblies within the scope of these descriptions, can be understood in view of FIGS. 7-9. In FIG. 7, the stent frame 400 of FIG. 3 in its neutral state is shown longitudinally aligned with a mandrel 700. The mandrel 700 has alternating lesser and greater diameter portions. In particular, the mandrel has circumferential channels 734 and 736 defining lesser diameter portions corresponding to the circumferential channels 434 and 436 of the stent frame 400 at the longitudinal positions of the inner prongs 112, 212 and 312 of the support rings 102, 202, 302.

The remainder of the mandrel 700 defines greater diameter portions corresponding to the remainder of the stent frame 400, particularly the longitudinal positions of the outer prongs 122, 222 and 322 of the support rings 102, 202, 302. The lesser diameter 710 of the mandrel at the lesser diameter portions defined by the circumferential channels 734 and 736 is greater than the inner diameter 110 of the stent frame 400 in its neutral state (FIGS. 3 and 7). Similarly, the greater diameter 720 of the mandrel at the greater diameter portions is greater than the outer diameter 420 of the stent frame 400.

Thus, the stent frame 400 and each support ring 102, 202 and 302 is diametrically expanded onto the mandrel 700 in FIG. 8. In the expanded state of FIG. 8, the stent frame 400 is ready for assembly with the graft 502 in a relatively taut condition of the graft. Once the graft is attached to the stent frame 400 in the expanded state, the stent frame 400 and graft 502 are removed from the mandrel as one piece, for example by removal of the mandrel from either longitudinal end of the stent frame 400 and graft 502. By resilient properties of the stent frame 400 and each support ring 102, 202 and 302, the stent frame 400 returns to the neutral state of FIG. 6, in which the waving state of the graft 502 is seen to show the billowing aspect of the major cover graft 502 as described with reference to FIG. 6.

The graft 502 generally maintains the support rings 102, 202 and 302 as approximately concentric with the longitudinal axis and spaced along the longitudinal axis as shown in FIG. 3 according to their longitudinal positions on the mandrel 700 when the graft 502 is attached.

Figure 10:
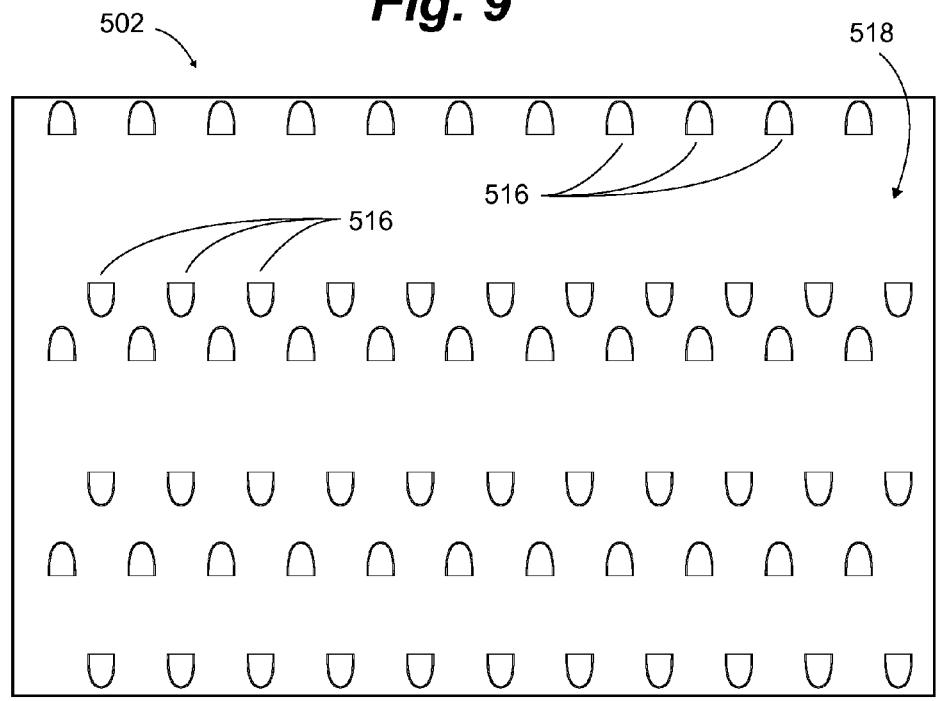
FIG. 10 is a view of the interior side of the graft of FIG. 5 showing pockets for support frame engagement according to at least one embodiment.

As shown in FIG. 9 and FIG. 10, in at least one embodiment the graft 502 includes pockets 516 along its interior side 518 (FIG. 10) at positions corresponding to the locations of the outer prongs 122, 222 and 322 in the diametrically expanded state of the stent frame 400 when mounted on the mandrel 700 as shown in FIG. 8. The pockets 516 receive the prong tips to maintain attachment of the graft 502 to the stent frame 400, for example as shown particularly in FIG. 9 with regard to the tips 124 of the outer prongs 122 of the support ring 102 and the tips 224 of the outer prongs 222 of the support ring 202. The graft 502 has circumferential excess relative to the circumference of the stent frame 400 prescribed by the outer diameter 320 when the neutral state of the stent frame is reached, for example upon removal from the mandrel 700. By registering the graft 502 with the stent frame 400 at discrete attachment points about the circumference of the interior side 518, the circumferential excess of the graft 502 is circumferentially distributed as waves as seen in the graft 502 in FIG. 6, and the billowing aspect of the major cover graft 502 is distributed and facilitated along its periphery.

Additionally, the graft 502 may be sewn to the stent frame 400 or attached in any other appropriate manner such as glue, suturing, lamination, or a mechanical fastener such as a clip. Thus, various attachment steps may be carried out while the, stent frame 400 and graft 502 are engaged with the mandrel 700.

These descriptions refer here to materials and making of the support ring 102, noting that the support rings 202 and 302 can be similarly made. In at least one embodiment, the support ring 102 is made of a memory shape wire, such as nitinol. Other biocompatible materials may be used. The memory shape wire is formed and heat treated in a fashion to create longitudinal and radial support. The ring 102 is formed such that the outer prongs 122 exert an outward radial force. In the illustrative embodiment, the outer prongs 122 exert a higher radial force than the inner prongs 112.

The variation in radial force may be accomplished in a variety ways. For example, the outer prongs 122 may have a different Austenite finish temperature ("Af") than inner prongs 112. To do so, the inner prongs 112 would be insulated/masked during a high temperature and time heat set-processing. The entire ring 102 would be heated to a certain temperature before the inner prongs 112 are masked or insulated. The outer prongs 122 would then be exposed to a more aggressive heat-set process to achieve a high radial force, while the masking of the inner prongs 112 would result in a lower radial force. In at least one embodiment, the high radial force area would have an Af<30 degrees Celsius and the lower radial force area would have an Af somewhere in the range of 35-39 degrees Celsius.

Another method of achieving the variation in radial force may be to electropolish the entire ring 102 up to a certain point. The outer prongs 122 may then be masked before further electropolishing of the inner prongs 112, thereby making the wire thinner in diameter in that section and resulting in a lower radial force. It should be appreciated that a combination of these two approaches may also be used. Additionally, in other embodiments, the radial force exerted by the outer prongs 122 may vary such that the force exerted by some of the outer prongs 122 is less than the force exerted by the inner prongs 112. Similarly, the radial force exerted by the outer prongs 122 may vary such that the force exerted by some of the inner prongs 112 is greater the force exerted by the outer prongs 122.

Whether made by these described materials and methods or others, the stent frame 400 is somewhat flexible, for example in order to stretch onto the mandrel 700, and is resilient so as to return to its neutral dimensions to facilitate the billowing aspect of the major cover graft 502. The flexible and resilient properties of the stent frame 400 also facilitate that the VDS assembly 500 conforms to shapes and dimensions of surrounding biological tissue in use while the side stents 532a and 532b are supported and localized within the longitudinal channels 434 between the cover graft 502 and the tissue.

A stent frame according to these descriptions as flexible and resilient so as to return to neutral dimensions refers both to diametrically contracting to neutral dimensions after being diametrically expanded and diametrically expanding to neutral dimensions after being diametrically compressed. For example, upon removal from the mandrel 700, the stent frame 400 diametrically contracts to neutral dimensions. Conversely, if diametrically compressed, the stent frame 400 is resiliently self-biased toward neutral dimensions and bears outward force upon any outer structure or tissue that constrains the stent frame 400 to less than its neutral diameter. This feature facilitates that a VDS stent assembly including such a frame conforms to anatomical dimensions to assure against endoleaks.

In at least one example, in which a first installed stent frame requires further support, a second self-expanding stent frame is inserted into the first self-expanding stent frame. For example, if anatomical dimension change over time after first installment of a frame-supported stent assembly, a second stent frame can be subsequently installed within the first stent frame. The second self-expanding stent frame then bears gentle outward force upon the interior of the first stent frame, further supporting the stent assembly, increasing the diameter of the first stent and urging it to conform to the new anatomical dimensions.

In the illustrated embodiment, the support ring 102 has eight (8) radial depressions 132 as shown in FIG. 2. The support rings 202 and 302 also have eight radial depressions each, such that the stent frame 400 has eight exterior longitudinal channels 432. In other embodiments, a stent frame otherwise within the scope of these descriptions can have more than or less than eight exterior longitudinal channels.

Support rings 102, 202 and 302 are illustrated as having the same inner diameters such that the stent frame 400 has the same inner diameter 110 defined by the inner prongs of each support ring. Similarly, support rings 102, 202 and 302 are illustrated as having the same outer diameters such that the stent frame 400 has the same outer diameter 120 defined by the outer prongs of each support ring. In other embodiments, the dimensions of support rings along the length of a stent frame can vary, for example to suit the various anatomies of different patients. In at least one embodiment, the inner diameter 110 of the stent frame 400 is approximately thirty (30) millimeters and the outer diameter 120 is approximately thirty eight (38) millimeters. While the stent frame 400 is illustrated to have three support rings as shown in FIG. 3, other embodiments of stent frames within the scope of these descriptions can have any number of support rings.

Referring now to FIGS. 5 and 6, the stent frame 400 is shown with a covering described as the major cover graft 502. This design and variations thereof are useful, for example, in endovascular reconstruction of the aorta wherever major aortic branches are involved. This includes the ascending aorta and the coronary arteries, the aortic arch and its branches, the thoracoabdominal aorta and the visceral arteries, the common iliac artery, and the hypogastric artery. Stent frames and grafts within the scope of these descriptions are useful in these and other anatomical regions.

The major cover graft 502 is used on the external surface of the stent frame 400. The graft 502 may be formed as covered Z stents, mesh wire, braided stents and other constructions of stent like material and biologically inert coverings (e.g. PTFE, polyester, ePTFE etc.) impermeable to blood and serum. The major cover graft 502 covers the stent frame 400 partially or completely along its length or circumference. Once the graft 502 is applied to the stent frame 400, the graft 502 defines walls of the exterior longitudinal channels 432 along which different branches of the aorta may be accessed and cannulated. The side stents 532a and 532b and other stents and grafts can be placed in fluid communication with central fluid flow channel 504. Thus, connections can be made through the major cover graft 502 to aortic branches such as coronary arteries, aortic arch branches, visceral branches and hypogastric arteries.

For example, in FIG. 5, a fenestration 510 is formed through the major cover graft 502 of the VDS assembly 500 to receive a vessel 512, which represents an artery such as a superior mesenteric artery (SMA) or a stent or stent graft. The fenestration 510 permits fluid flow from the central fluid flow channel 504 to enter the vessel 512, defining a lateral flow channel 514 through the major cover graft 502 at the fenestration 510 and along the vessel 512. Such fenestrations may be located anywhere along the graft 502 where technically feasible with respect to the support rings within the graft. In the illustrated embodiment, the fenestration 510 is located at the front center of the frame. The fenestration 510 and other fenestrations formed to access fluid communication with the central fluid flow channel 504 may have various diameters and may be shaped as circular, oval, or other shapes. In the illustrated embodiment, the fenestration 510 represents an opening formed through the material of the major cover graft 502 in a location that does conflict with the support rings of the stent frame. In particular, the fenestration 510 is formed at a longitudinal and circumferential location between outer prongs 222 of the longitudinally central support ring 202 of the three support rings 102, 202 and 302 of the support frame 300. The fenestration 510 for an SMA vessel, stent, or graft is formed at a circumferential location corresponding to the radially flat portion 450 of the stent frame 400.

While the stent frame 400 is illustrated to have three support rings as shown in FIG. 3, other embodiments of stent frames within the scope of these descriptions can have any number of support rings. Furthermore, while the support ring 102 has alternating inner prongs 112, outer prongs 122, radial depressions 132, and a radially flat portion 150, other embodiments of support rings within the scope of these descriptions can have other geometric configurations.

Figure 11:
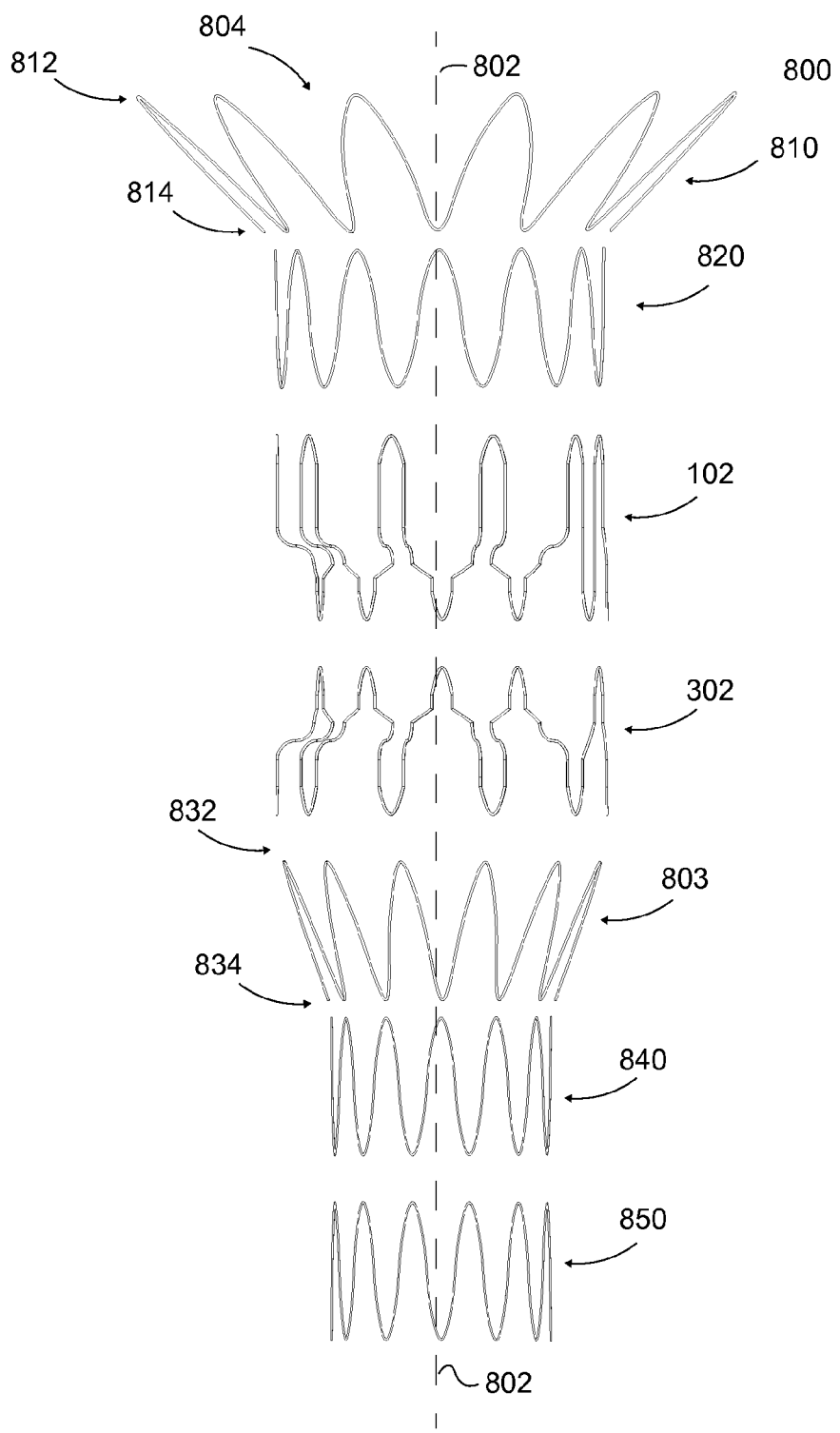
FIG. 11 is an elevation view of a VDS frame according to at least one other embodiment.

For example, a stent frame 800 according to at least one embodiment is shown in FIG. 11. The stent frame 800 includes, in order from top to bottom in the drawings, a first frustoconical support ring 810, a first single diameter support ring 820, the support ring 102, the support ring 302, a second frustoconical support ring 830, a second single diameter support ring 840, and a third single diameter support ring 850. The stent frame 800 is configured to support a multi-path stent assembly having a longitudinal axis 802 along which a central fluid flow channel 804 is defined for blood flow in a downstream direction from a first end defined by the first frustoconical support ring 810 to a second end defined by the third single diameter support ring 850. The stent frame 800 advantageously has a first diameter reduction at the first frustoconical support ring 810 and a second diameter reduction at the second frustoconical support ring 830, such that flow along the central fluid flow channel 804 may be reduced by one or more flow channels that branch from the central fluid flow channel 804 in a stent assembly supported by the stent frame 800. In at least one embodiment, the first longitudinal end of the stent frame 800 defined by the first frustoconical support ring 810 constitutes the cranial end of the stent frame 800 with reference to human anatomy, and the second longitudinal end defined by the third single diameter support ring 850 constitutes the caudal end of the stent frame 800.

The first frustoconical support ring 810 is formed as a Z-stent having a first end 812 with a diameter greater than that of a second end 814. The first end 812 is defined by turning points of the Z-stent extending outward from the longitudinal axis 802. The second end 814 is defined by turning points of the Z-stent extending inward from the longitudinal axis 802.

The single diameter support ring 820 is formed as a Z-stent in which turning points are equidistant from the longitudinal axis 802. The support ring 102 and the support ring 302 are detailed in the preceding descriptions with reference to FIGS. 1-3.

The second frustoconical support ring 830 is formed as a Z-stent having a first end 832 with a diameter greater than that of a second end 834. The first end 832 is defined by turning points of the Z-stent extending outward from the longitudinal axis 802. The second end 834 is defined by turning points of the Z-stent extending inward from the longitudinal axis 802.

The single diameter support rings 820, 840, and 850 are formed as Z-stents in which respective turning points are equidistant from the longitudinal axis 802, defining a single respective diameter for each ring. The second and third single-diameter support rings 840 and 850 are illustrated having the same diameter in the stent frame 800. The first single diameter support ring 820 is illustrated as having greater diameter than the second and third single-diameter support rings 840 and 850, which are downstream of the diameter-reducing second frustoconical support ring 830 relative to the first single diameter support ring 820.

Figure 16:
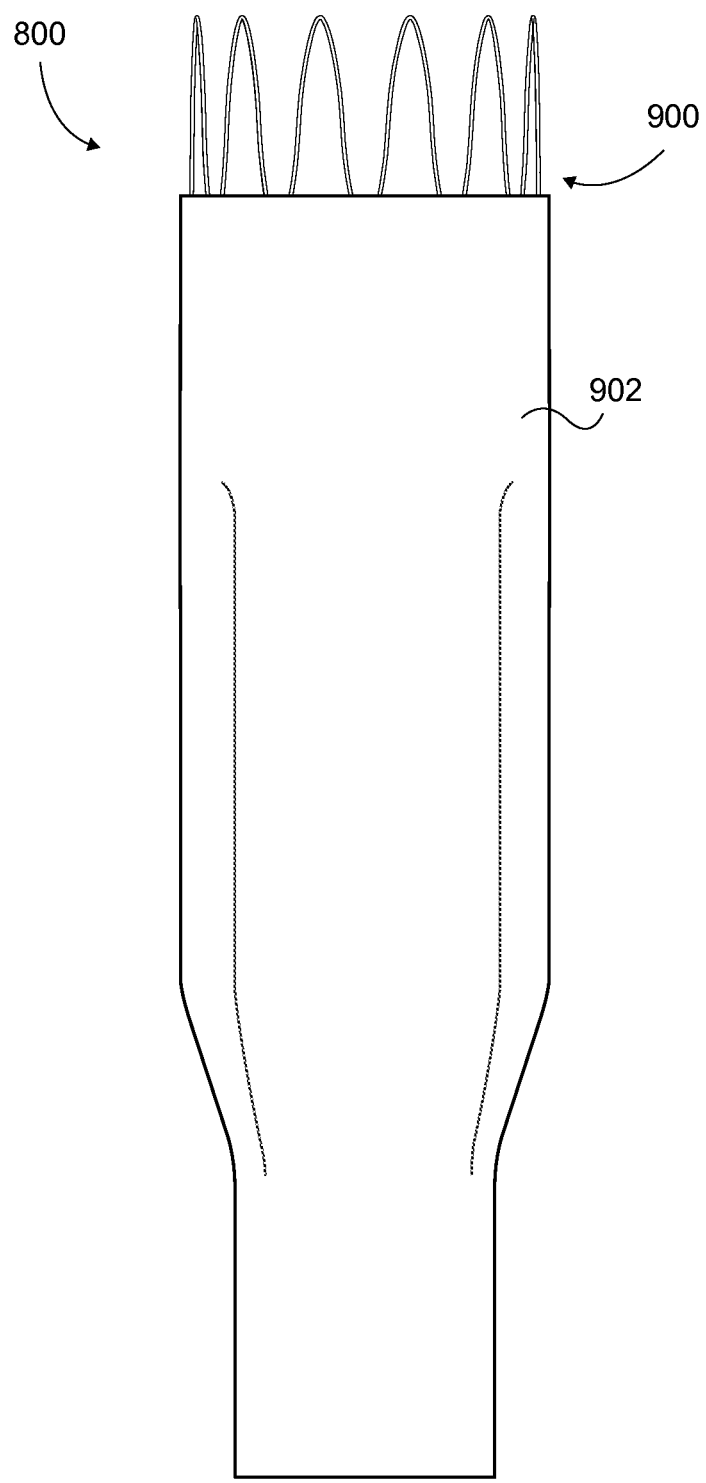
FIG. 16 is an elevation view of a stent assembly that includes the VDS frame of FIG. 11 and a covering without fenestrations according to at least one embodiment.
Figure 17:
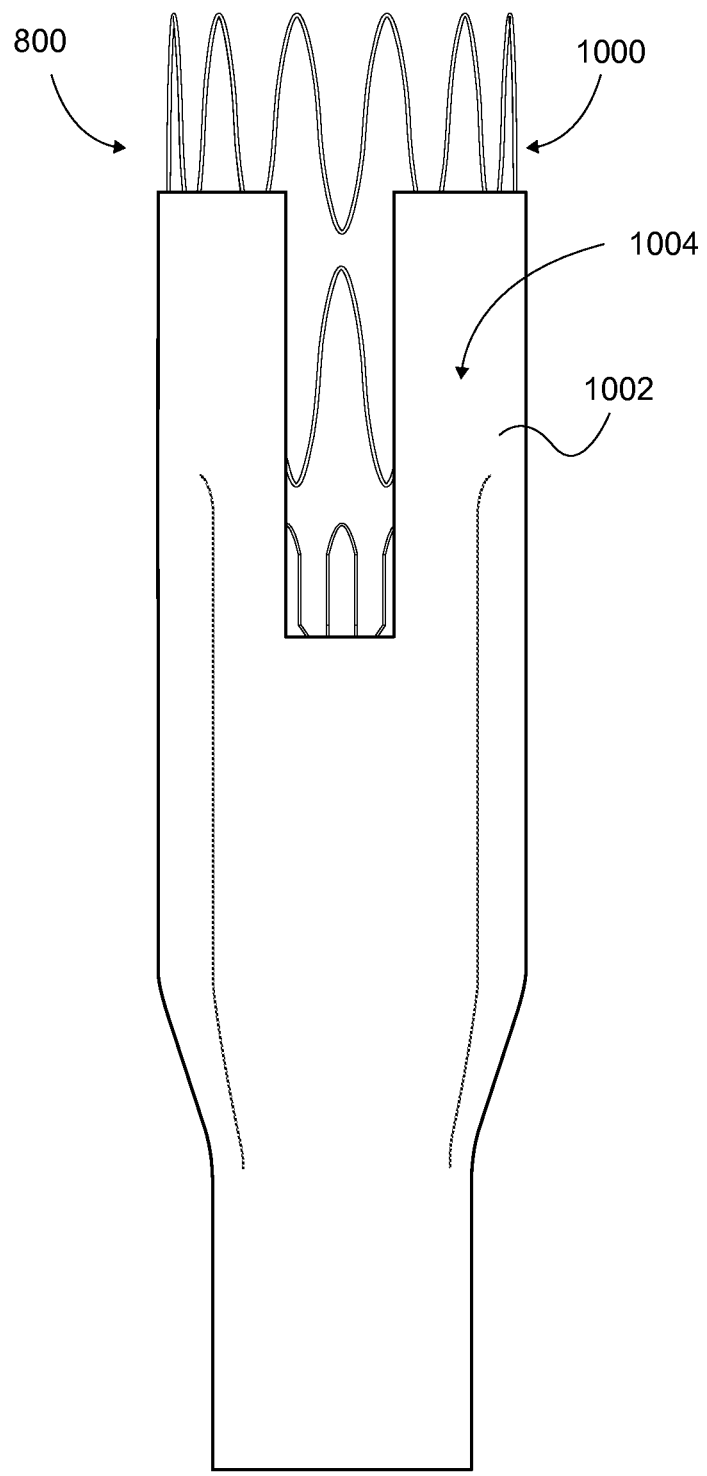
FIG. 17 is an elevation view of a stent assembly that includes the VDS frame of FIG. 11 and a covering with a single fenestration according to another one embodiment.
Figure 18:
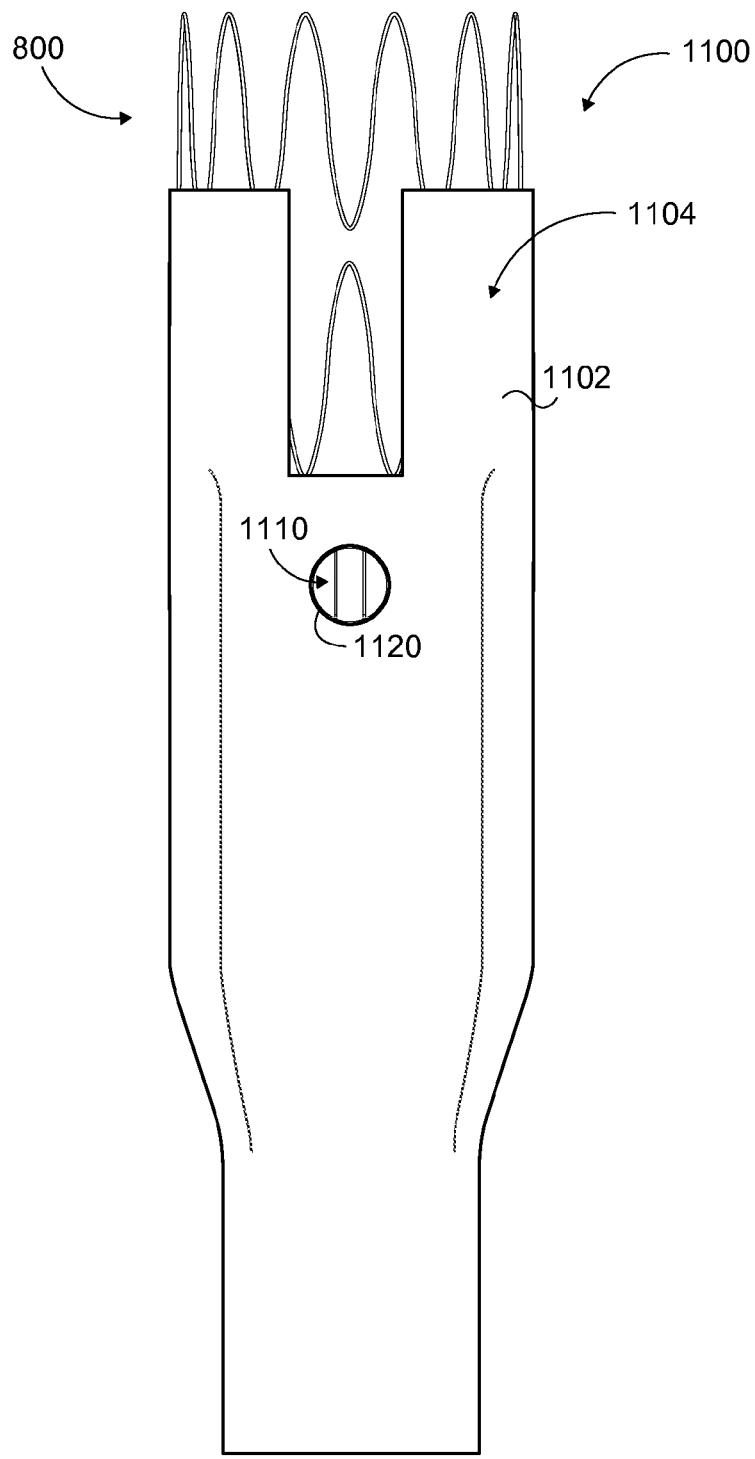
FIG. 18 is an elevation view of a stent assembly that includes the VDS frame of FIG. 11 and a covering with a multiple fenestrations according to yet another one embodiment.

Similar to the way the stent frame 400 of FIG. 3 can be covered with the major cover graft 502, the stent frame 800 can be covered with a variety of coverings, at least three of which are represented in FIGS. 16-18. In each, the illustrated upper end represents the upstream longitudinal end of the stent assembly, and the illustrated lower end represents the downstream longitudinal end. In use, each serves as an endograft in which blood flows downstream through the longitudinal central channel of the stent assembly from a greater diameter upstream end to a lesser diameter downstream end, and one or more branches may direct blood flow from the central channel. For use in the aorta, the upstream end constitutes the cranial end of the stent frame 800 with reference to human anatomy, and the downstream end constitutes the caudal end of the stent frame 800.

Figure 12:
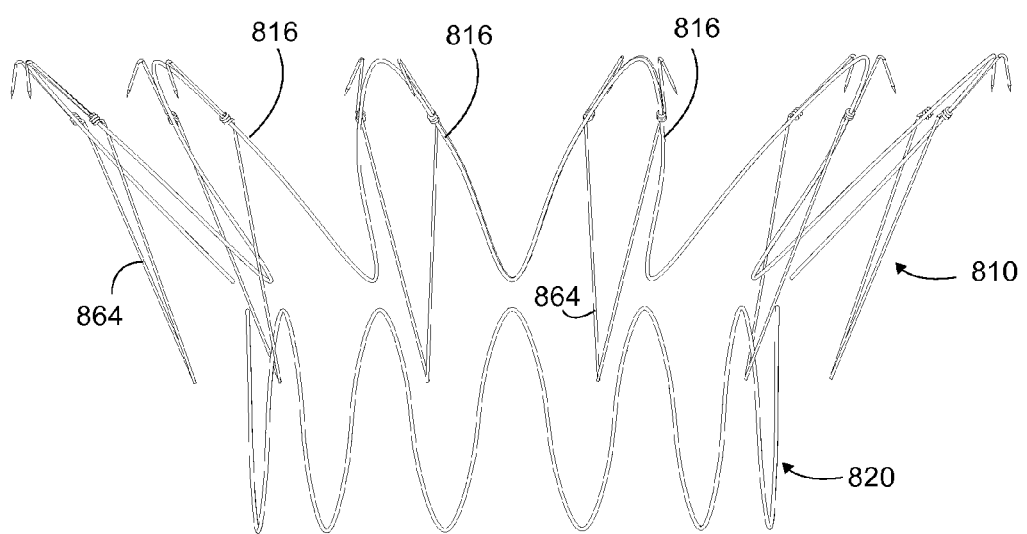
FIG. 12 is a perspective view of an upper portion of the VDS frame of FIG. 11 with barbed stabilizing elements according to at least one embodiment.
Figure 13:
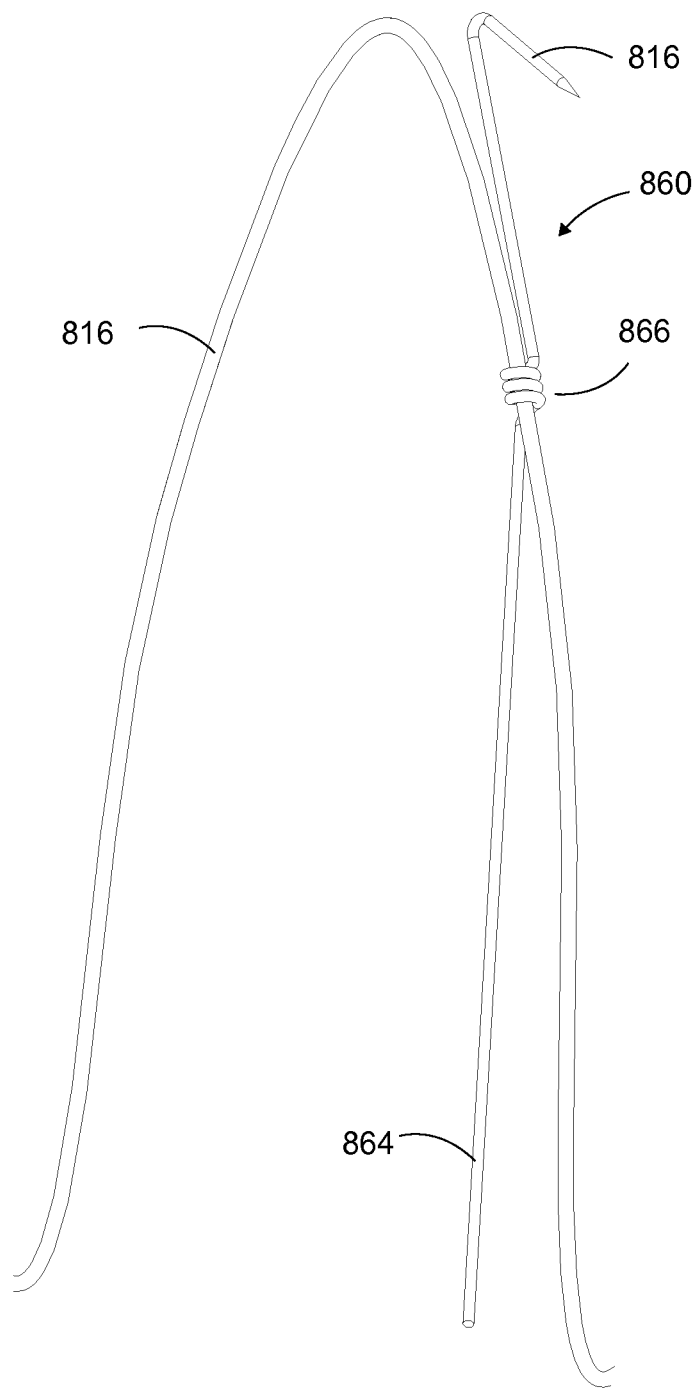
FIG. 13 is a close-up view of a portion of the VDS frame of FIG. 11 with a barbed stabilizing element of FIG. 12.
Figure 14:
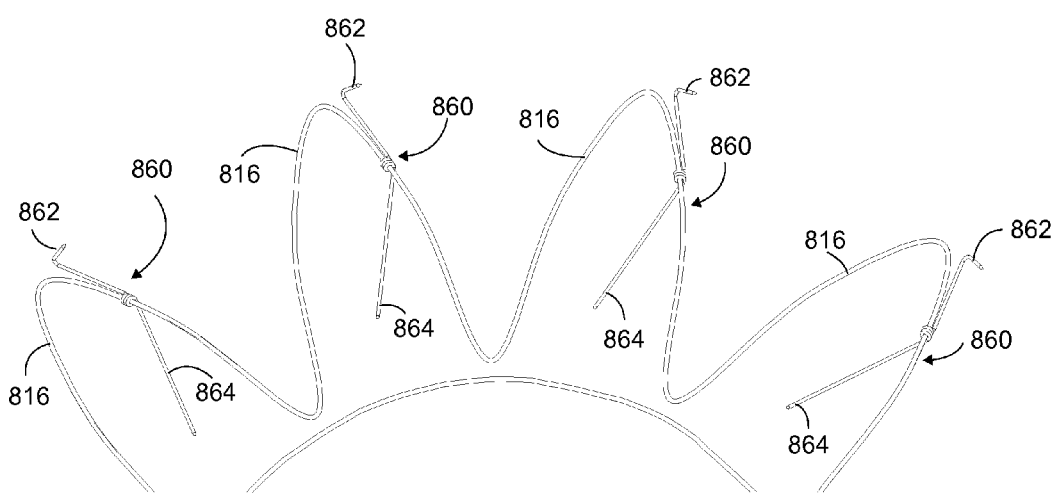
FIG. 14 is another close-up view of a portion of the VDS frame of FIG. 11 with the barbed stabilizing elements of FIG. 12.

To attach the upstream end of the stent frame to host tissue, stabilizing elements may be connected to the first frustoconical support ring 810 as shown in FIGS. 12-15. As shown in FIG. 12, stabilizing elements 860 extending from the upstream end of the support ring 810 define a crown for engaging tissue. As shown in FIGS. 13 and 14, each stabilizing element 869 is wrapped around a respective prong 816 of the support ring 810 and formed from memory shape wire or stainless steel wire. Each stabilizing element 860 includes a barb 862 or hook that is uncovered and serves to fixate the endograft and add stability against the aortic wall.

Figure 15:
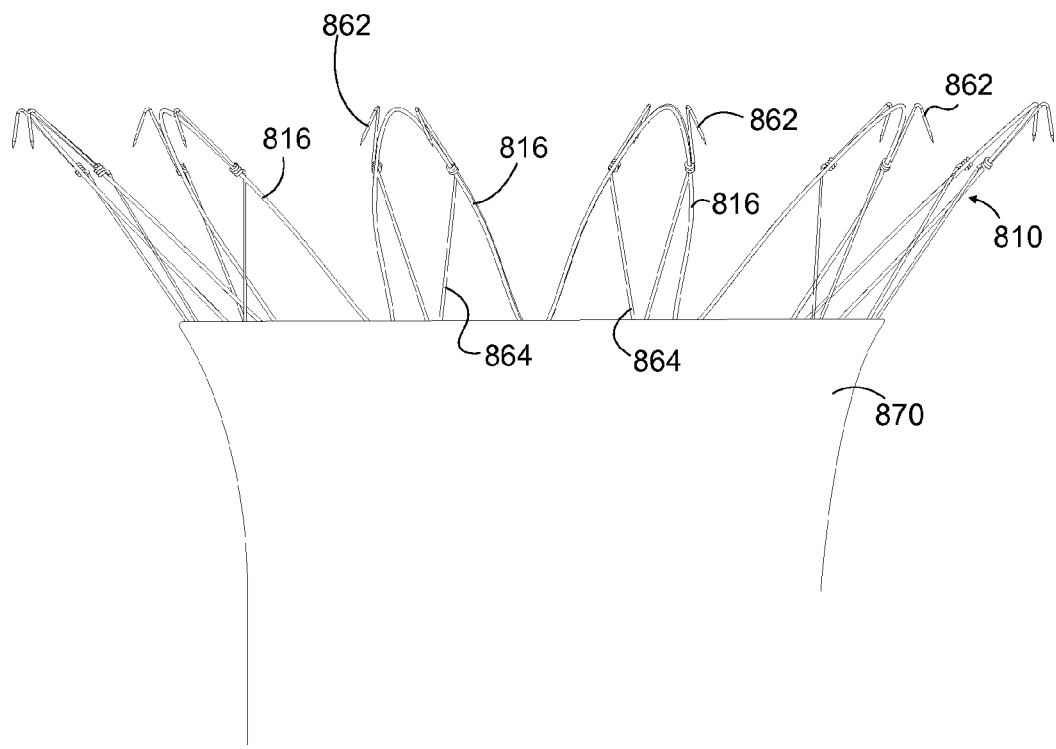
FIG. 15 is an elevation view of the VDS frame portion of FIG. 11 with the barbed stabilizing elements and a covering material.

Each stabilizing element 860 also includes a limb 864 (FIG. 13) that is covered by the covering material 870 in FIG. 15. As shown in FIG. 13-14, the limb 864 is positioned between the prongs 816 of the support ring 810. The attachment point 866 of the stabilizing element 860 acts as a fulcrum for the limb 864. In use, the barbs 862 engage the aorta, while the limbs 864 push outward against the covering material 870 as shown in FIG. 15 to seal the covering material 870 against the aorta. In that way, the limbs 864 act as biasing elements. The covering material 870 represents, for example, the upper end of any one of the coverings shown in FIGS. 16-18.

Each stabilizing element 860 may be formed separately from stainless steel or other metal. It can be laser cut in whole together with the support ring 810. The stabilizing elements 860 may be individually wrapped around a prong 816. The shape of the element 860 as depicted allows for one end of the wire to "hook" into the aortic wall, thereby stabilizing the device and preventing migration of the endograft. The caudal end of the limb 864 will have an eccentrically directed angle and this portion of the wire will be located on the inside aspect of the graft coverage, in this embodiment the PTFE. By positioning the caudal end of the limb 864 at an angle in between each pair of prongs 816, the endograft coverage will be pushed externally against the aortic wall to create additional points of contacts and seal. In addition, if the limbs 864 are captured towards the center of the graft with the delivery system, they can restrain the top stent and make the device easier to control.

In FIG. 16, a stent assembly 900 includes the stent frame 800 and a covering 902 sheathing the stent frame. The covering 902 is shown without any fenestrations. In this embodiment, the stent assembly 900 can be used below the kidney vessels.

In FIG. 17, a stent assembly 1000 includes the stent frame 800 and a covering 1002 sheathing the stent frame. The covering 1002 is shown with a single fenestration 1004 illustrated as a rectangular slot in the cranial end of the covering 1002. The slot has an open cranial end 1006 such that the upper edge of the covering 1002, interrupted by the open cranial end of the slot, partially surrounds the frame 800. In this embodiment, the stent assembly 1000 can be used for aneurysms below the superior mesenteric artery (SMA). In such use, the single fenestration 1004 is used for both celiac artery and SMA stents or grafts.

In FIG. 18, a stent assembly 1100 includes the stent frame 800 and a covering 1102 sheathing the stent frame. A first fenestration 1104 is illustrated as a rectangular slot in the cranial end of the covering 1102, in which the slot has an open cranial end 1106 such the upper edge of the covering 1102, interrupted by the open cranial end of the slot, partially surrounds the frame 800. A second fenestration 1110 is illustrated as a circular hole in the covering 1102. In this embodiment, the stent assembly 1100 can be used for aneurysms below the celiac artery. In such use, the first fenestration 1104 and the separate second fenestration 1110 are used respectively as separate access fenestrations for the celiac artery and SMA stents or grafts. In FIG. 18, a portion of the far side of the stent frame is visible through the fenestration 1110

In FIG. 18, a fenestration support ring 1120 surrounds the second fenestration 1110. The fenestration support ring 1120 can be, for example, an eight (8) millimeter diameter ring formed from nitinol or other biocompatible materials, or can be constructed, for example, as described below with reference to FIG. 19. Placed around the second fenestration 1110 in FIG. 18, the fenestration support ring 1120 in at least one use receives and stabilizes the fenestration support of a branch in fluid communication with the stent assembly 1100 such as an SMA vessel or an SMA stent or graft.

The fenestration support ring 1120 may also serve as a radio-opaque marker during the placement procedure of the stent assembly 1100. In such use, the fenestration support ring 1120 serves as "point zero" for the positioning and deployment of the stent assembly 1100, or any stent assembly in which the fenestration support ring 1120 is included. Advantageously, the fenestration support ring 1120 for such use can be constructed of or with materials visible under X-ray or other medical imaging techniques.

Figure 19:
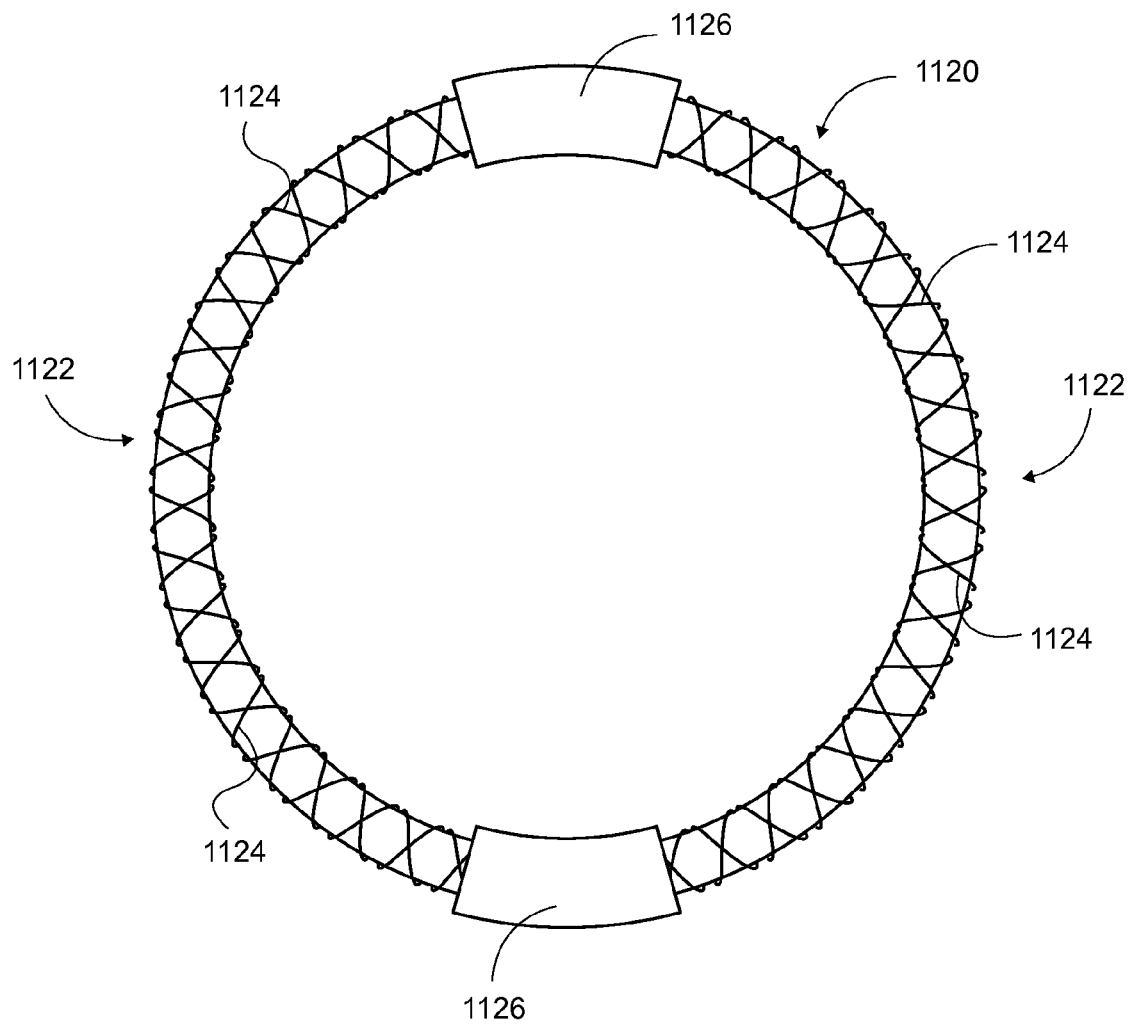
FIG. 19 is a plan view of a fenestration support ring according to at least one embodiment.

A particular exemplary construction for the fenestration support ring 1120 is represented in FIG. 19. The fenestration support ring 1120 constructed as illustrated can serve as a radio-opaque marker. The fenestration support ring 1120 in this embodiment includes two supports 1122 formed as half-circles from a memory shape wire. Nitinol and/or other materials with the similar properties can be used to form the half-circle supports. The supports 1122 are wrapped with singular or multiple turns 1124 of a thin radio-opaque marker material such as platinum. The supports 1122 are connected by crimping their ends with connectors 1126. In the illustrated embodiment, each connector 1126 is formed from gold, which also acts as a radio-opaque marker. In that way, the connectors 1126 and turns 1124 are visible on an x-ray image. The fenestration support ring 1120 therefore illustratively stabilizes the fenestration 1110 and makes the fenestration visible on an x-ray image. The marker 1120 may be connected to the frame 800 via glue or other adhesive, stitching, or heat treatment.

Figure 20:
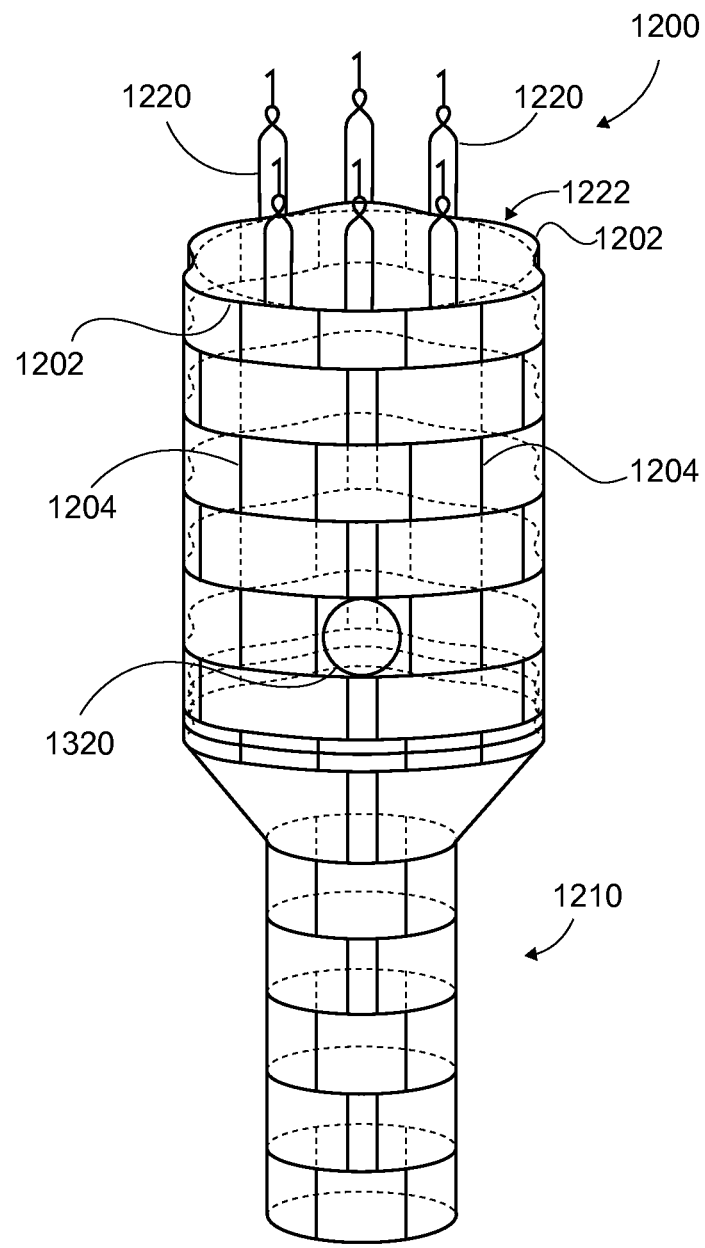
FIG. 20 is a perspective view of a stent frame according to at least one embodiment.
Figure 21:
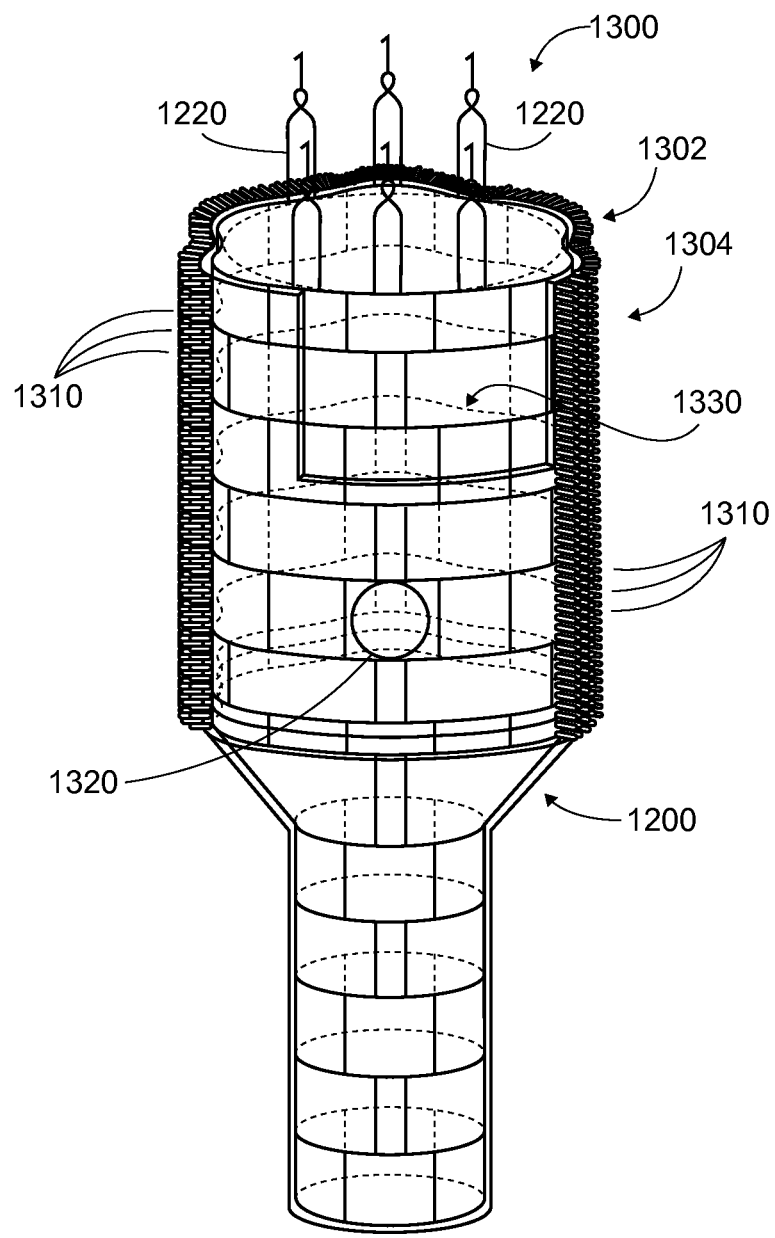
FIG. 21 is a perspective view of an endograft stent assembly that includes the stent frame of FIG. 20 and the graft material at least partially covered by microfibers or thrombogenic material according to at least one embodiment.

FIG. 20 is a perspective view of a stent frame 1200 according to at least one embodiment. FIG. 21 is a perspective view of an endograft stent assembly 1300 that includes the stent frame 1200 at least partially covered by a graft 1304. The design and geometrical shape of the endograft stent assembly 1300 permits separate access to the renal arteries, thus facilitating use with many anatomical variations of juxtarenal and suprarenal aneurysms. The design allows for placement of parallel covered renal stents while reducing the likelihood of an endoleak along the renal stents, and reduces the risk of kinking and compression of the renal stents. When the outside of a graft is covered or partially covered with fibers of thrombogenic material, the external force that parallel stents exert on the graft and its thrombogenic material creates longitudinal grooves that seal along the parallel stents.

The stent frame 1200 can be constructed of a metal alloy, including a memory shape wire such as nitinol. Other biocompatible materials may be used. In at least one example, the memory shape wire is cut and heat treated in a fashion to create longitudinal and radial support. The stent frame 1200 includes circumferential wires 1202 shaped to define circumferential waves that are aligned longitudinally to define longitudinal channels. A radial variation is defined between the crests (radial maxima) and nadirs (radial minima) of the circumferential waves. In at least one example, the radial variation is approximately three (3) millimeters. In other examples, the radial variation may be in the range of two to four (2-4) millimeters. The circumferential distance between the crests can be, for example, in the range of three to fifteen (3-15) millimeters. Like the stent frame 400 that includes a radially flat portion 450 (FIG. 3), the stent frame 1200 has a radially flat portion for locating an SMA vessel, stent, or graft that branches from the interior of the endograft stent assembly 1300.

The stent frame 1200 includes longitudinal wires 1204 that extend between the circumferential wires. Each circumferential wire 1202 is spaced, for example at 5-20 mm, from the next and has a wave shape to define the longitudinal channels. The circumferential positions of the longitudinal wires 1204 alternate in a staggered fashion.

The endograft stent assembly 1300 includes a fenestration support ring 1320, which, in the illustrative embodiment, is an 8 mm nitinol ring. The fenestration support ring 1320 is positioned or created within the stent frame 1200 with its center point at approximately thirty four (34) millimeters below the top edge 1302 of the stent 1300. The fenestration support ring 1320 in at least one use receives the visceral or SMA stent placed during the placement procedure. The fenestration support ring 1320 also serves as "point zero" for the positioning and deployment of the endograft stent assembly 1300. A second ring (not shown) may be positioned cranial of the SMA fenestration support ring 1320, with its center approximately fifteen (15) millimeters cranial to the fenestration support ring 1320. The center of the second ring may be at 12:30 clock position relative to the SMA fenestration support ring 1320, and the diameter of the second ring may measure between eight and ten (8-10) millimeters.

The stent frame 1200 may be formed as one unit. In at least one embodiment the stent frame 1200 approximately one hundred (100) millimeters in longitudinal length. The proximal aspect of the stent frame 1200 is wavy tubular extending thirty four (34) millimeters proximal to the center point of the visceral or SMA fenestration support ring 1320. The distal aspect extends fourteen (14) millimeters below the center point of the SMA fenestration support ring. At this level, the stent frame 1200 includes a distal extension 1210 that funnels to eighteen (18) millimeters or more in diameter over a distance of ten to twenty (10-20) millimeters. This distal extension 1210 is approximately fifty to sixty (50-60) millimeters long, with at least the most distal forty (40) millimeters measuring at least eighteen (18) millimeters in diameter. In at least one embodiment, the most anterior portion of the proximal part of this stent frame 1200 is curved flat and does not have any waves or channels.

As shown in FIGS. 20 and 21, the stent frame 1200 includes a crown of barbed stents 1220 extending from its top edge 1222 at its most cranial aspect. In the endograft stent assembly 1300, the barbed stents 1220 are uncovered and serve to fixate the endograft stent assembly and add stability against the aortic wall. Each barbed stent 1220 is formed of memory shape wire. In one embodiment, the barbed stents 1220 are formed in a figure-of-eight fashion with the top of the component containing a hook facing the external surface of the stent. In another embodiment, the hook may be attached to the proximal end of a wire. The middle of the wire is equipped with a small round hole for placement of a trigger wire. The barbed stents 1220 are shaped to extend outwards to a 45 degree angle on the horizontal plane upon deployment.

In the illustrated embodiment of FIG. 21, the graft 1304 is partially covered with microfibers or other thrombogenic material 1310 along the 3 and 9 o'clock aspects of it, with the center of the fenestration support ring 1320 defining 12 o'clock. The microfibers 1310 assist in filling any remaining gutters as a source of endoleak along parallel renal stents. In other embodiments, hydrogel or other sealing materials may be used to coat the external surface of the endograft in order to fill in any gutters alongside the parallel renal stents. A fenestration 1330 is defined by the graft 1304 as a rectangular slot in the cranial end of the graft, in which the slot has an open cranial end. A second fenestration is illustrated as a circular hole in the graft 1304 in a location corresponding to the SMA fenestration support ring 1320. In use, the fenestration 1330 and the separate second fenestration are used respectively as separate access fenestrations for the celiac artery and SMA stents or grafts.

Figure 22:
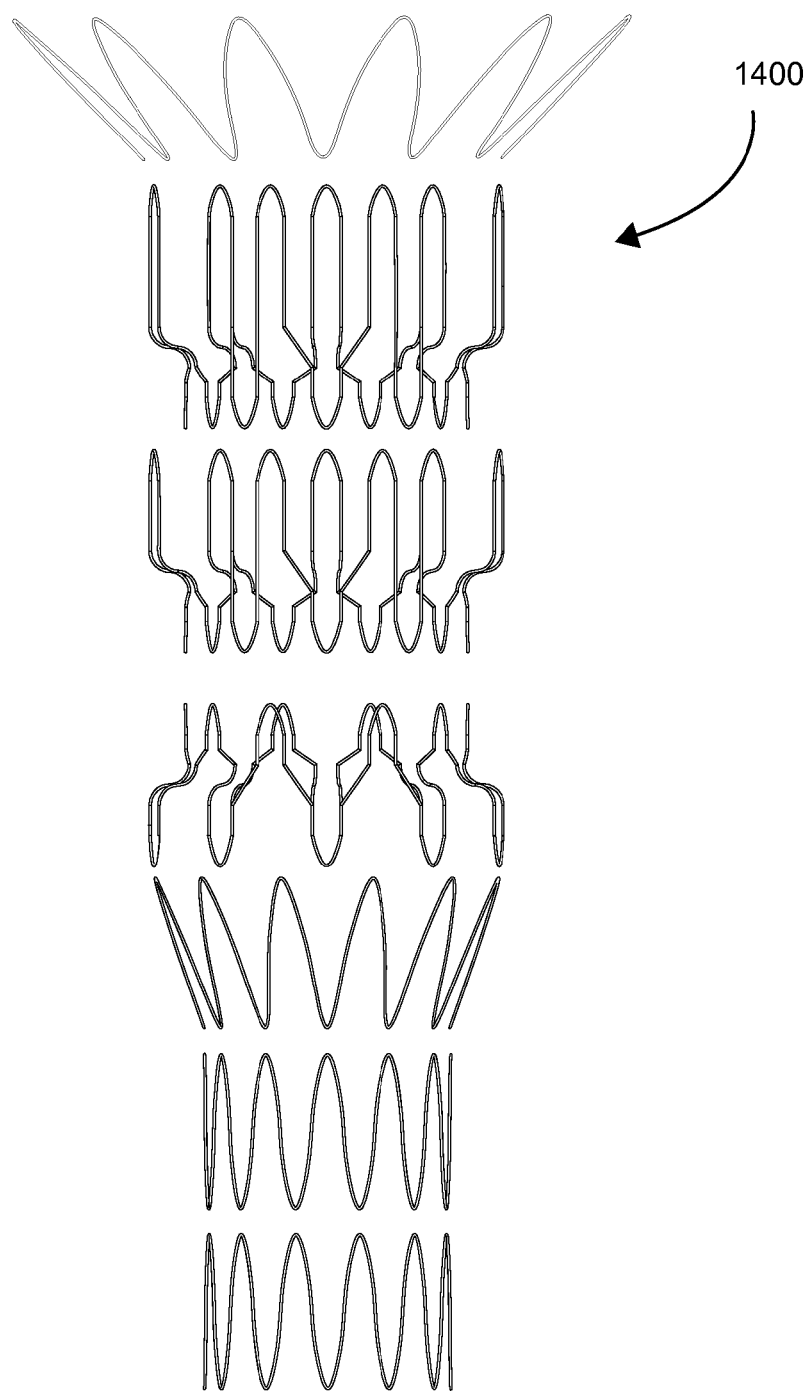
FIG. 22 is a perspective view of another stent frame according to at least one embodiment.
Figure 23:
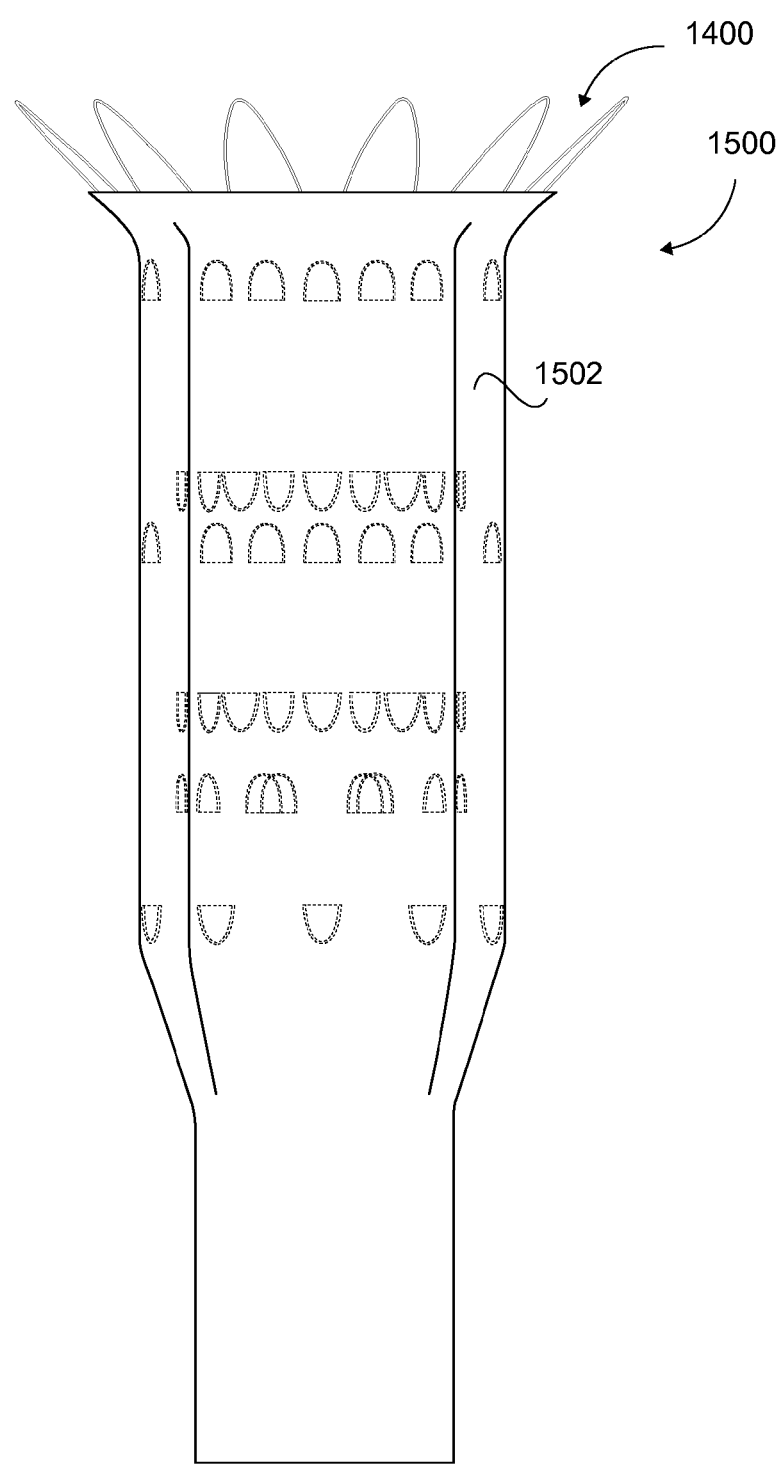
FIG. 23 is a perspective view of an endograft stent assembly that includes the stent frame of FIG. 22 at least partially covered by a graft.

FIG. 22 is a perspective view of a stent frame 1400 according to at least one embodiment. FIG. 23 is a perspective view of an endograft stent assembly 1500 that includes the stent frame 1400 at least partially covered by a graft 1502.

FIGS. 24 through 28 illustrate components of an iliac limb assembly 1600. All dimensions given in these descriptions correspond at least to one embodiment without limiting the scope of these descriptions to one such embodiment.

Figure 24:
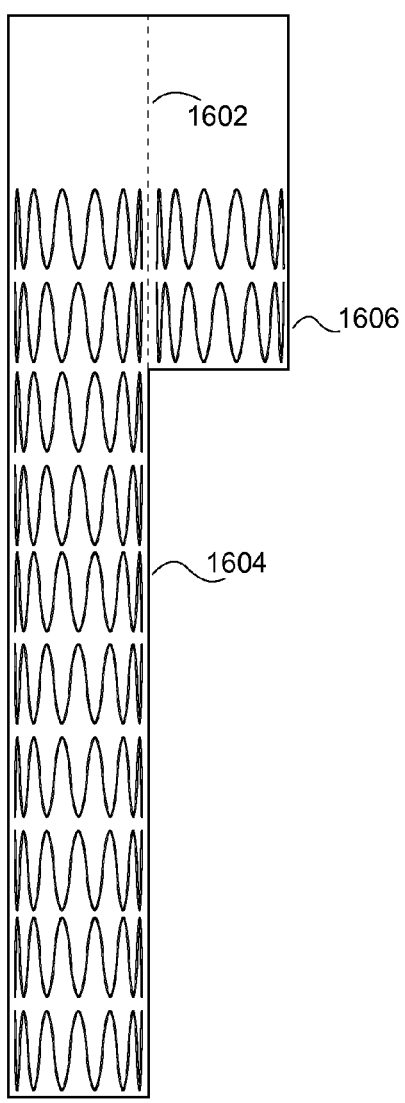
FIG. 24 is an elevation view of a divided upper stent tube and two lower stent tubes of different length according to at least one embodiment.
Figure 25:
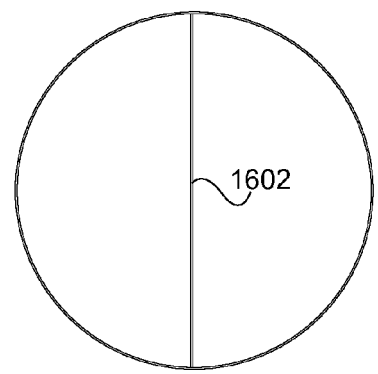
FIG. 25 is a longitudinal end view of the stent tubes of FIG. 24 showing a septum dividing the upper stent tube according to at least one embodiment.

In FIGS. 24 and 25, a dual channel tubular stent is shown including graft material, such as ePTFE, supported by Z-stents. The dual channel stent has two internal channels separated longitudinally by a septum 1602, for example for a distance of five (5) millimeters or more. The septum 1602 is shown in longitudinal end view in FIG. 25. The diameter of the upstream dual channel part of the tubular stent is twenty six (26) millimeters to twenty eight (28) millimeters in at least one example. The main tube divides, for example after the first five (5) millimeters, into two approximately cylindrical tubes 1604 and 1606, one longer than the other, each measuring approximately thirteen (13) millimeters in diameter in at least one example. The longer tube 1604 extends in at least one example for a distance of at least one hundred (100) millimeters. The shorter tube 1606 extends in at least one example for approximately twenty (20) millimeters. In at least one particular use, the longer tube 1604 constitutes a first iliac limb stent for connecting a first side or channel of the dual channel tubular stent to a first iliac artery. In that example, the shorter tube 1606 constitutes a junction by which a second iliac limb stent 1608 (FIG. 8), for connection to a second iliac artery, can be connected to the second side or channel of the dual channel tubular stent.

Figure 26:
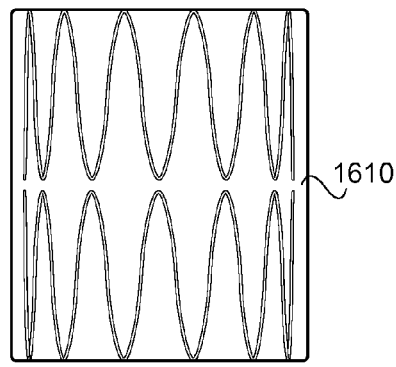
FIG. 26 is an elevation view of a graft tube reinforced with Z stents according to at least one embodiment.
Figures 27, 28:
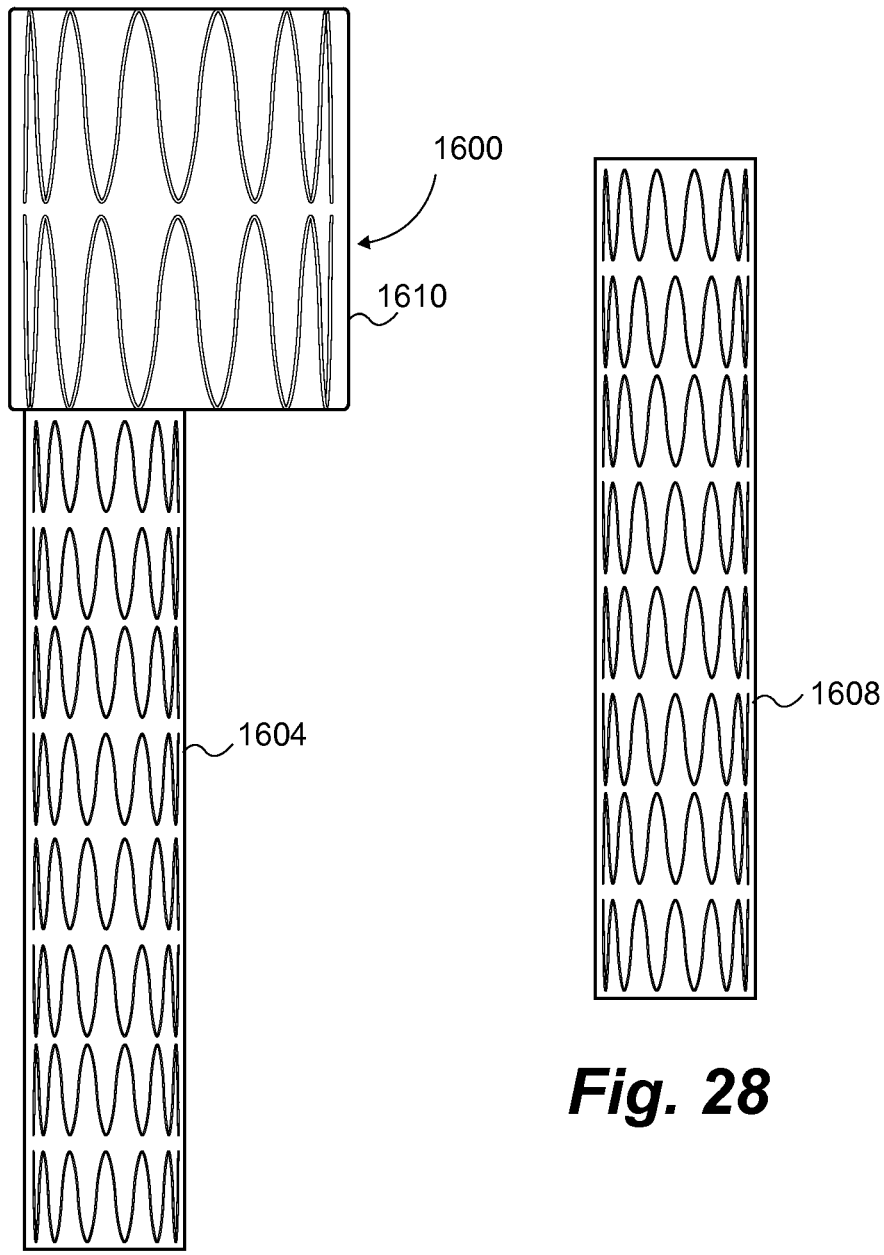
FIG. 27 is an elevation view of a bifurcated stent system, according to at least one embodiment, including the stent tubes of FIG. 24 and the graft tube of FIG. 26.
FIG. 28 is an elevation view of a second limb stent for engagement with the shorter tube of FIG. 24 according to at least one embodiment.

A graft tube 1610 reinforced with Z stents is shown in FIG. 26. Combining the structures of FIGS. 24 and 26, by placing the graft tube 1610 (FIG. 26) around the upstream dual channel part of the tubular stent (FIG. 24) produces an iliac bifurcation device 1600 (FIG. 27) that can be moved cranially and caudally within the main body of the endograft 1500 shown in FIG. 23. This will help in controlling and adjusting the location of the placement of the iliac limb stents 1604 and 1608 in the iliac arterial system. FIG. 28 shows the second iliac limb stent 1608 for engagement with the shorter tube 1606 in FIG. 24.

By placing the iliac bifurcation at a maximum cranial location possible within the iliac limb system as illustrated and described here, there is room to move the second iliac limb stent 1608 up or down and adjust the desired length remaining for engagement with an iliac artery. The two flow channels for the two iliac limb stents 1604 and 1608 are separated by the septum 1608 throughout the upstream dual channel part of the tubular stent. The septum 1602 prevents the upstream cranial end of the second iliac limb stent 1608, as the position of the stent 1608 is adjusted, from obstructing the flow entering the first iliac limb stent 1604 on the other side of the septum 1602. This permits a range of human anatomy dimensions to be served by one set of components (FIGS. 24-28).

Figure 29:
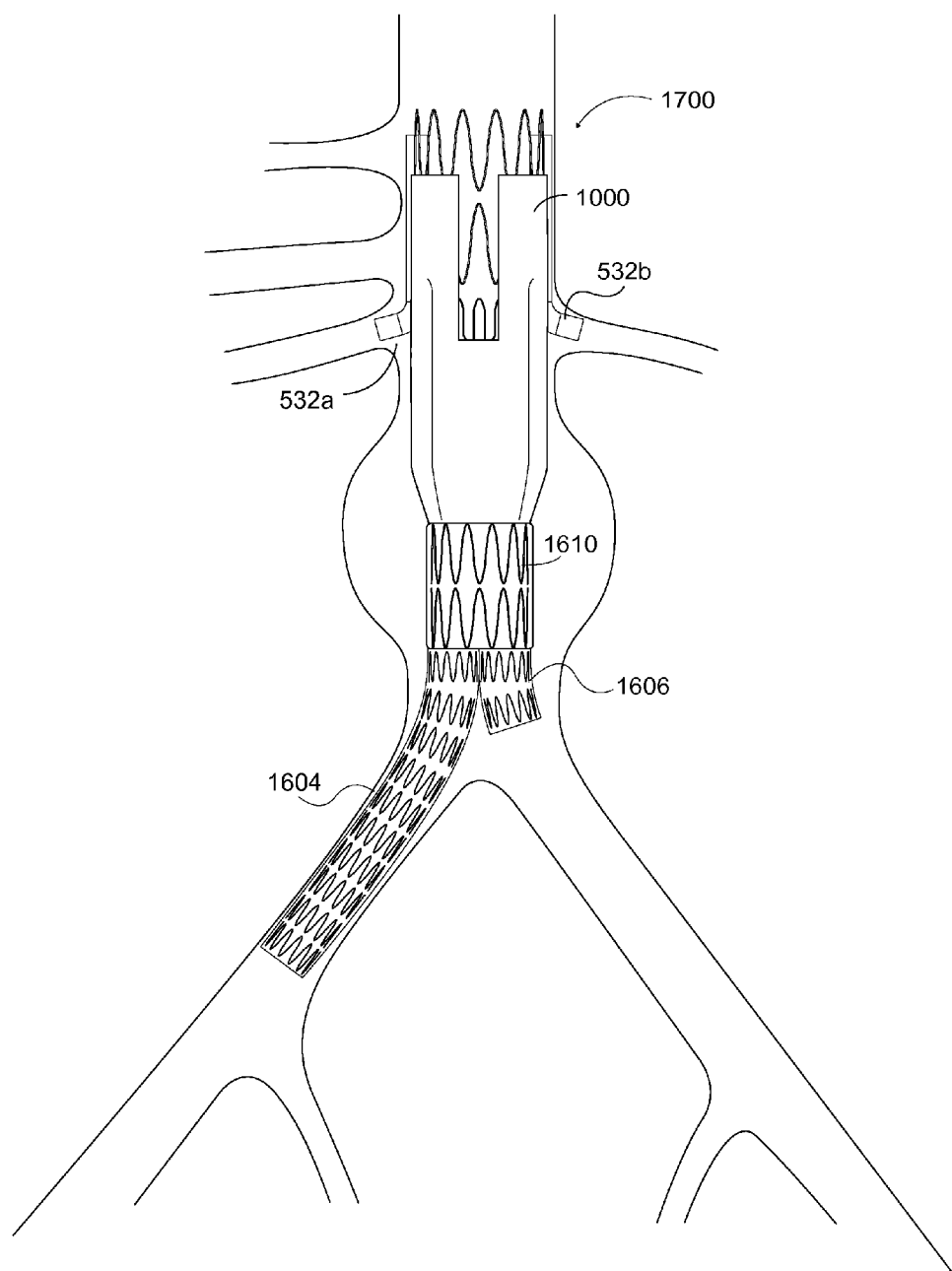
FIG. 29 is an elevation view of a multi-branch stent assembly according to at least one embodiment.
Figure 30:
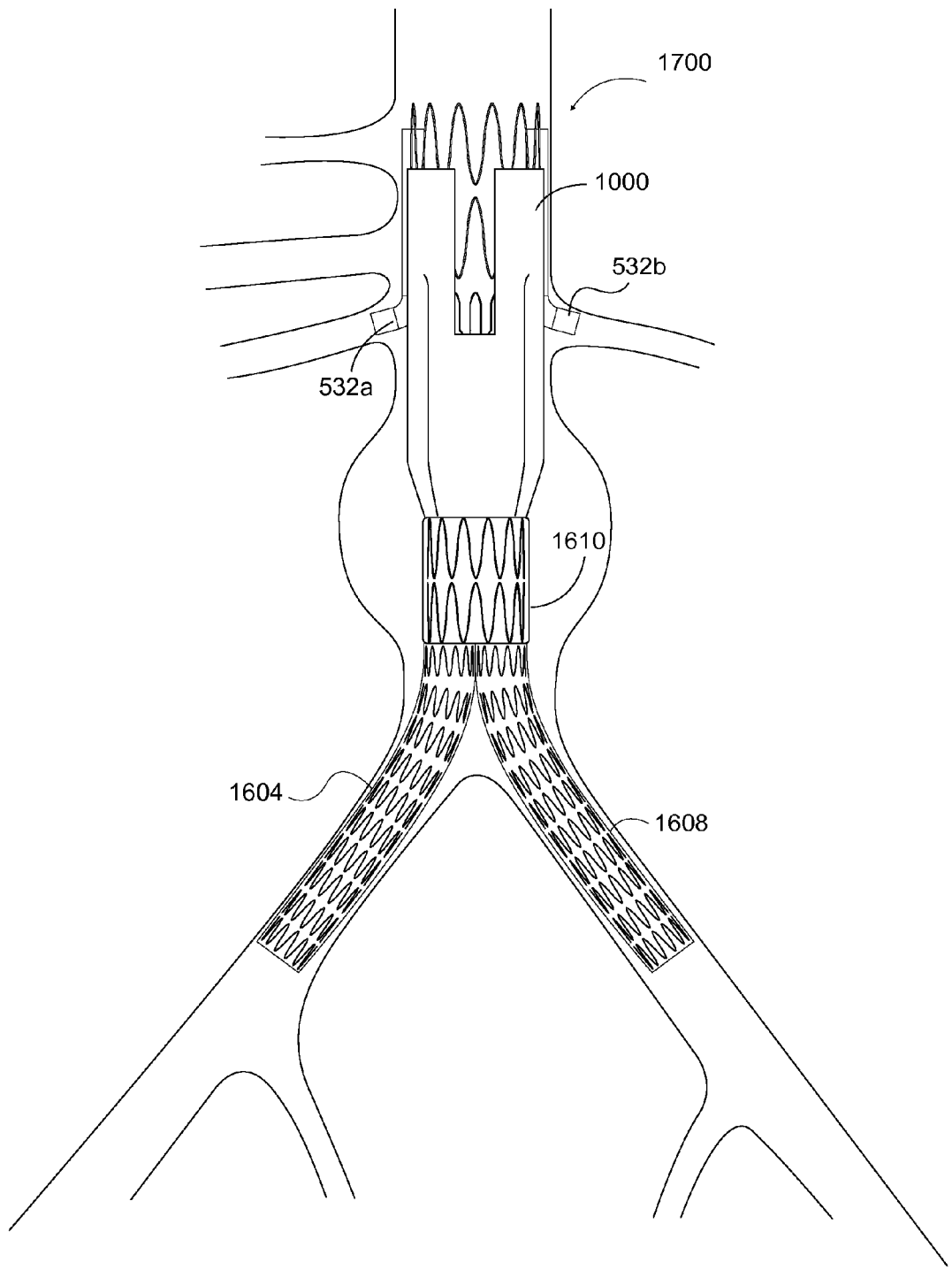
FIG. 30 is an elevation view of the multi-branch stent assembly of FIG. 29 in use with the second iliac limb stent of FIG. 28.

FIG. 29 illustrates a multi-branch stent assembly 1700 in a state of partial assembly or installation, with the longer first iliac limb stent 1604 in engagement, at its caudal downstream end, with a first iliac artery. FIG. 30 illustrates the multi-branch stent assembly 1700 of FIG. 29, in use in a human aorta, with the second iliac limb stent 1608 in engagement, at its caudal downstream end, with the second iliac artery. In FIGS. 29 and 30, the multi-branch stent assembly 1700 includes the stent assembly 1000 of FIG. 17.

To achieve the installation shown in FIG. 30, the stent assembly 1000 is first installed. In at least one such example, a fenestration support ring or other radio-opaque marker serves as "point zero" for the positioning and deployment of the stent assembly 1000, during the placement procedure in order to properly place the stent assembly for engagement with the anatomical SMA and celiac artery.

Lower portion of side stents 523*a* and 523*b* are then engaged with the renal arteries as shown in FIG. 30, with upper longitudinal portions of the side stents 523*a* and 523*b* cradled within and supported by the exterior longitudinal grooves of the stent assembly 1000.

Subsequent to installation of the stent assembly 1000, the first iliac limb stent 1604 can be positioned in different locations by the telescoping engagement of the upstream end of the dual channel tubular stent with the downstream end of the stent assembly 1000. The adjustable telescoping engagement of the dual chamber stent with the stent assembly 1000 defines a functional length adjustment for the first iliac limb stent 1604 relative to the engage first iliac limb artery. The position of the dual chamber tubular stent is selected to engage the first iliac limb stent 1604 with the first iliac limb artery. Once the engagements of FIG. 29 are achieved as desired, the second iliac limb stent 1608 can be engaged with the second iliac artery as shown in FIG. 30.

Thus, an endovascular device (endograft) for treatment of complex abdominal aneurysms involving the kidney vessels is provided. The device can go above the kidney vessels, while blood flows to the kidneys and the gut vessels are preserved. In the parallel endograft technique in which stents 523*a* and 523*b* are installed alongside the aortic endograft, the aortic endograft does not crush the kidney stents or create gutters that may otherwise cause leaks of blood alongside the grafts. These are advantages of these variable depression stent (VDS) and billowing graft assemblies.

Figure 31:
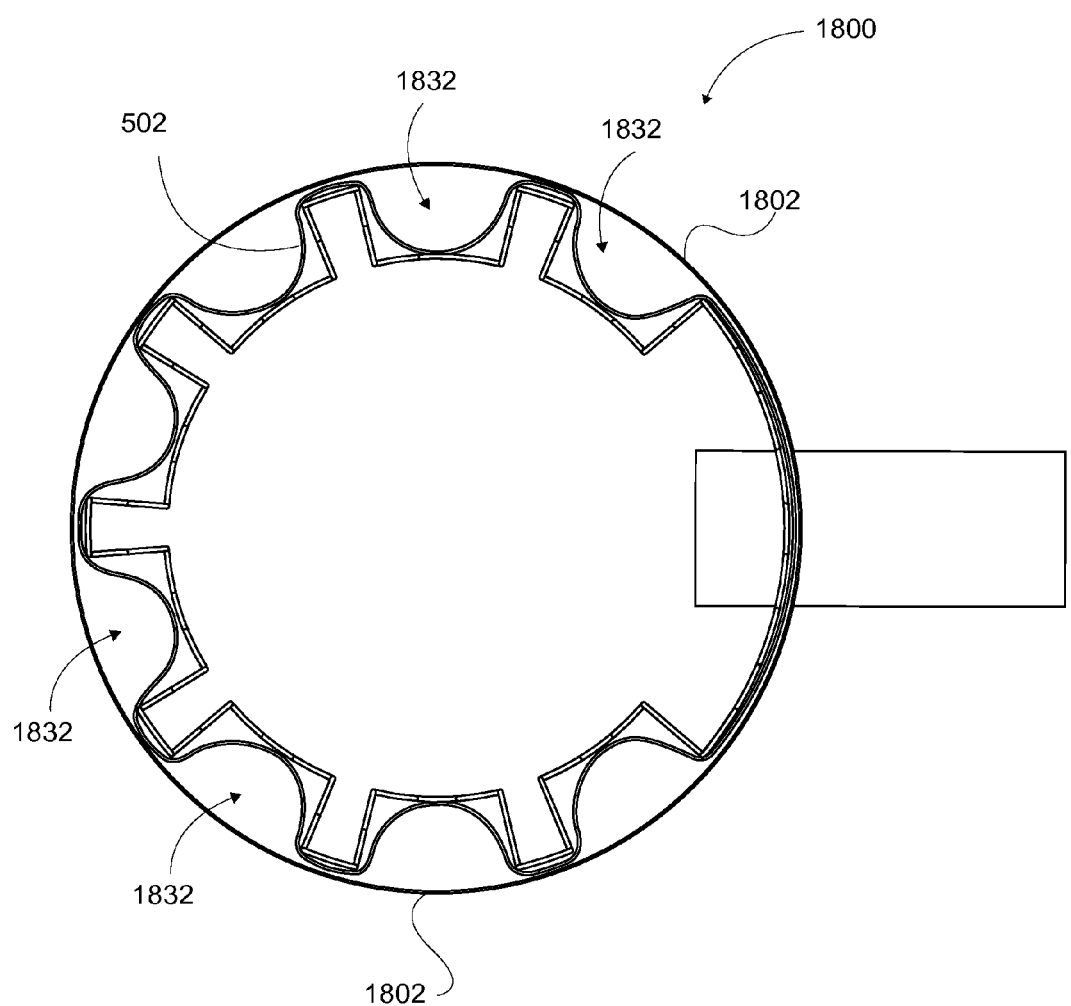
FIG. 31 is a longitudinal end view of a stent assembly according to yet another embodiment in which multiple longitudinal channels defined by a first circumferential graft are covered to form tunnels by a second circumferential graft.

FIG. 31 is a longitudinal end view of a tunneled graft stent assembly 1800 according to yet another embodiment in which multiple longitudinal channels defined by a first circumferential graft are covered by a second circumferential graft 1802 to form tunnels. In FIGS. 5 and 6, open longitudinal channels 432 are defined along the exterior of the graft 502, and the longitudinal side stents 532a and 532b may be laterally supported by the aortic wall in some uses. In FIG. 31, the graft 502 is further covered by a second graft 1802 and covered longitudinal tunnels 1832 are defined between the inner graft 502 and outer graft 1802. The covered longitudinal tunnels 1832 may constitute stents or receiving stents therein in FIG. 31 in lieu of, for example, the longitudinal side stents 532a and 532b in FIGS. 5 and 6. In the tunneled graft stent assembly 1800, parallel flow channels defined in the longitudinal tunnels don't require further lateral support and thus the tunneled graft stent assembly 1800 may be placed within an aneurysm.

Figure 32:
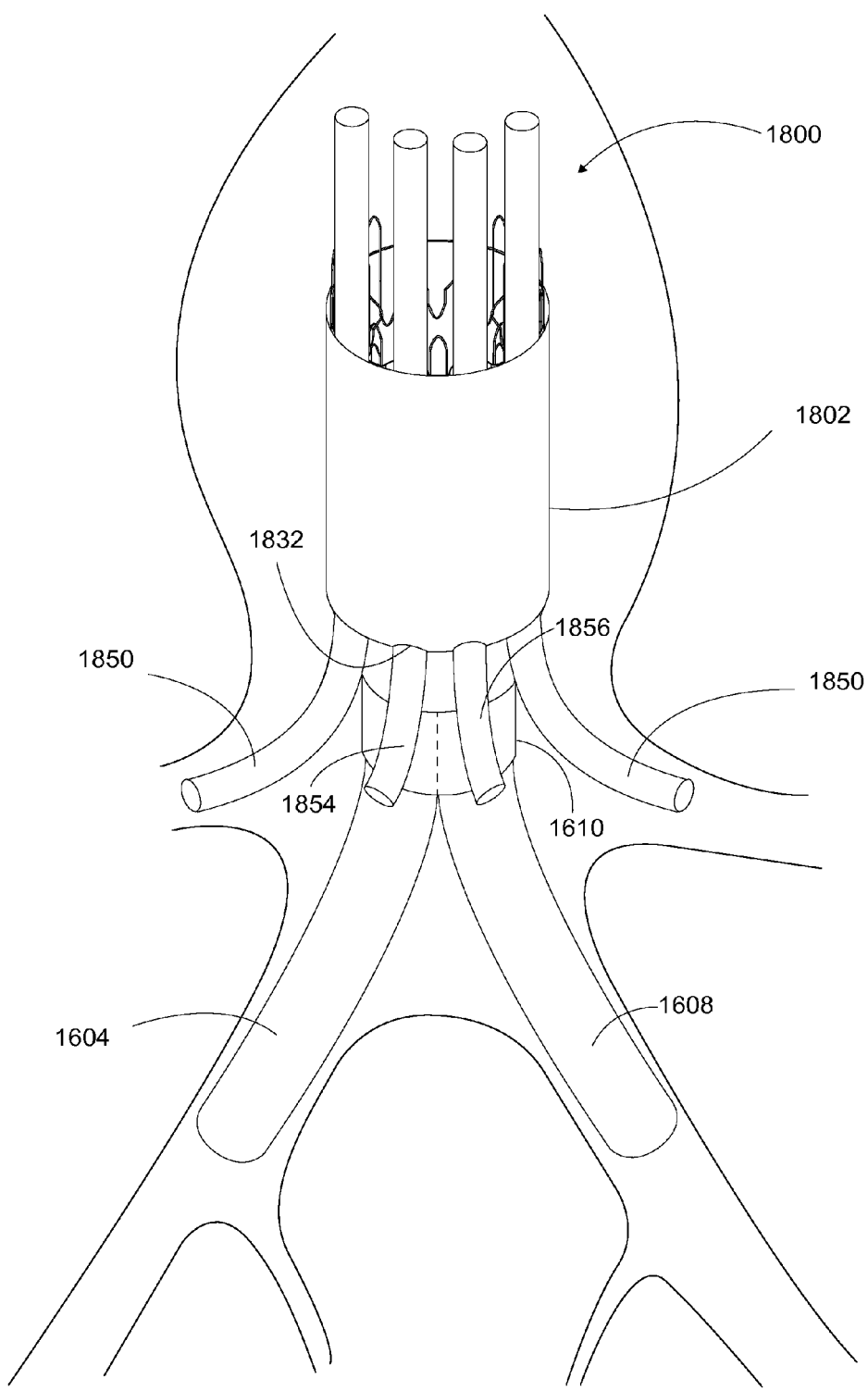
FIG. 32 is a view of the stent assembly of FIG. 31 positioned in an artery for use in treating a thoracoabdominal aneurysm.

As illustrated in FIG. 32, device 1800 is shown for thoracoabdominal device placement. As illustrated, device 1800 is placed in a thoracoabdominal area and renal stents 1850 are extending into the tunnels 1832, and the celiac 1854 and SMA 1856 are also received within the device. Members 1608 interconnect the iliac arteries as previously described. In this manner, the parallel stents 1850 don't need lateral support and this allowed the device 1800 to be placed in the middle of an aneurysm.

Figure 33:
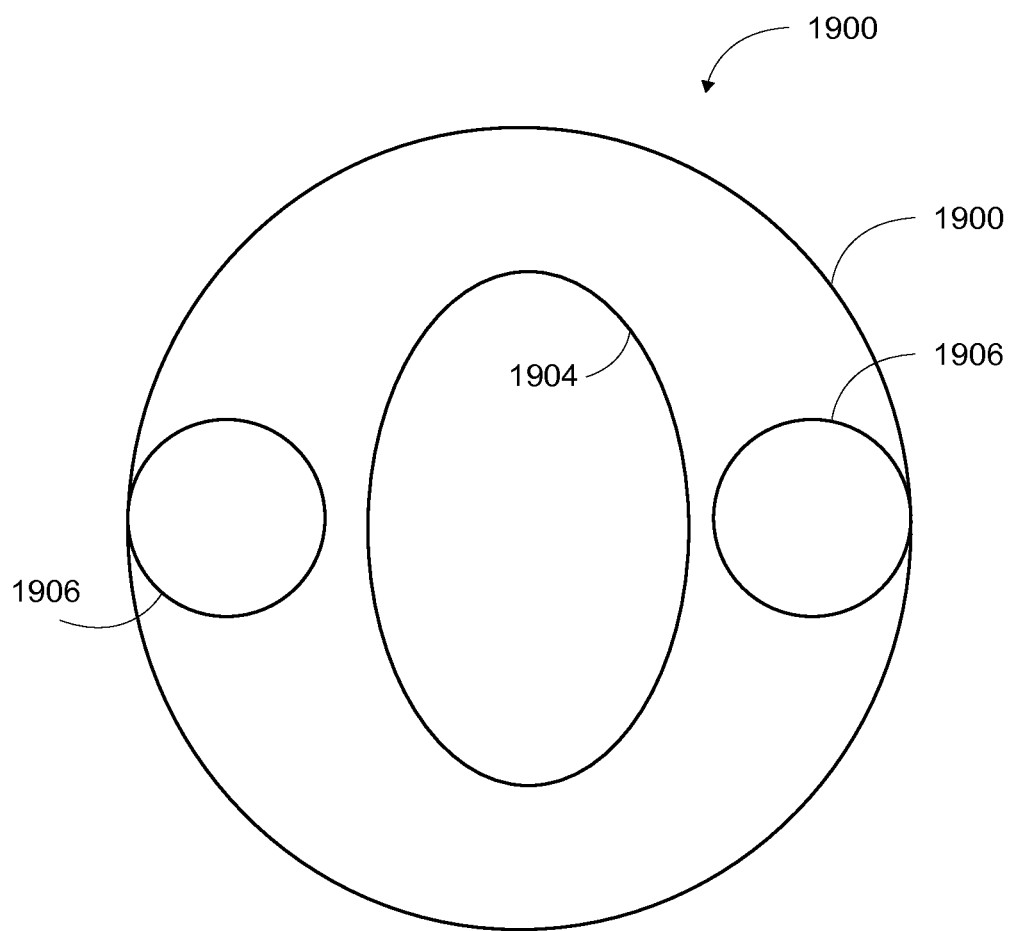
FIG. 33 is a longitudinal end view of a stent assembly with an inflatable seal component according to at least one embodiment.

FIG. 33 is a longitudinal end view of a stent assembly 1900 with an inflatable seal component 1902 according to at least one embodiment. In at least one example, the stent assembly 1900 has an inflatable component 1902 on a graft 1904. The inflatable component 1902 has a deflated state and an inflated state. The assembly 1900 with one or more inflatable seal components 1902 can be put in place, with the inflatable component 1902 in its deflated state, together with parallel stents 1906. When the assembly 1900 is placed, and the inflatable seal component 1902 is inflated as shown in FIG. 33, longitudinal grooves are formed around the parallel stents 1906. The infusion of the inflatable component 1902 with special polymers while the parallel stents 1906 are in place will create longitudinal grooves along the parallel stents 1906 after the polymers harden inside the inflatable component 1902.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

What is claimed is:

1. A stent assembly comprising:
    a first support ring having interconnected circumferentially alternating first inner prongs and first outer prongs, the first inner prongs defining a first inner diameter around a central longitudinal axis, and the first outer prongs defining a first outer diameter around the central longitudinal axis greater than the first inner diameter;
    a second support ring spaced from the first support ring along the central longitudinal axis, the second support ring having interconnected circumferentially alternating second inner prongs and second outer prongs, the second inner prongs defining a second inner diameter around the central longitudinal axis, and the second outer prongs defining a second outer diameter around the central longitudinal axis greater than the second inner diameter;
    longitudinal channels defined between an inner prong of the first support ring and an inner prong of the second support ring;
    a billowing graft engaging at least a portion of one or more of the first support ring and the second support ring, the billowing graft when in a relaxed state follows a waving peripheral path along the longitudinal channels at least partially around at least one of the first support ring and second support ring, wherein the billowing graft engaging the first support ring and the second support ring at about the longitudinal channels creates longitudinal grooves, wherein at least two of the longitudinal grooves extend in a direction that is parallel to a direction of a central axis extending along a length of the stent assembly,
    wherein the at least two of the longitudinal grooves extend between the first support ring and the second support ring and define an outwardly extending planar shelf between the at least two of the longitudinal grooves and along a length of the billowing graft.

2. The stent assembly according to claim 1, wherein:
    a circumferential position of a particular first inner prong is aligned with a circumferential position of a particular second inner prong;
    circumferential positions of two first outer prongs adjacent the particular first inner prong are aligned respectively with circumferential positions of two second outer prongs adjacent the particular second inner prong such that the at least one longitudinal channel is defined along the aligned circumferential positions of the particular first inner prong and particular second inner prong.

3. The stent assembly according to claim 2, wherein the billowing graft billows along one or more longitudinal channels creating the one or more longitudinal grooves in the relaxed state.

4. The stent assembly according to claim 2, wherein the billowing graft is selectively attached to the two first outer prongs adjacent the particular first inner prong and to the two second outer prongs adjacent the particular second inner prong.

5. The stent assembly according to claim 4, wherein the billowing graft is free to billow radially outward from the particular first inner prong along the longitudinal groove in response to pressurization from fluid flow therein.

6. The stent assembly according to claim 1, further comprising at least one side stent positioned at least partially along the billowing graft within the longitudinal groove.

7. The stent assembly according to claim 1, wherein;
    the first inner prongs have bodies directed in a first radial direction; and
    the first outer prongs have bodies directed in a second radial direction opposite the first radial direction.

8. The stent assembly according to claim 7, wherein the first support ring further has a portion defined by at least two prongs that extend in opposite radial directions, the portion of the first support ring being equidistant from the central longitudinal axis.

9. The stent assembly according to claim 8, wherein the first outer prongs and the at least two prongs of the portion of the first support ring are equidistant from the central longitudinal axis.

10. The stent assembly according to claim 8, wherein the second support ring further has a portion defined by at least two prongs that extend in opposite radial directions, the at least two prongs of the portion of the second support ring being equidistant from the central longitudinal axis.

11. The stent assembly according to claim 10, wherein the portion of the first support ring has a circumferential position aligned with a circumferential position of the portion of the second support ring.

12. The stent assembly according to claim 11, wherein an angle subtended partially around the central longitudinal axis by the portion of the first support ring is approximately equal to an angle subtended partially around the central longitudinal axis by the portion of the second support ring.

13. The stent assembly according to claim 12, wherein the angle subtended partially around the central longitudinal axis by the portion of the first support ring is less than one hundred and eighty degrees.

14. The stent assembly according to claim 13, wherein:
the first inner prongs and first outer prongs are connected together by intermediate connecting segments; and
the first inner prongs, first outer prongs and intermediate connecting segments together subtend a summation angle of greater than one hundred and eighty degrees around the central longitudinal axis.

15. The stent assembly according to claim 13, wherein:
the first support ring comprises a first portion including the first inner prongs and first outer prongs in radially opposite direction and a second portion including the first inner prongs and first outer prongs radially flat; and
the first portion of the first support ring is C-shaped and subtends an angle of greater than one hundred and eighty degrees around the central longitudinal axis.

16. The stent assembly according to claim 1, wherein:
the second inner prongs have bodies directed in the first radial direction; and
the second outer prongs have bodies directed in the second radial direction opposite the first radial direction.

17. The stent assembly according to claim 1, wherein:
the second outer prongs have bodies directed in the first radial direction; and
the second inner prongs have bodies directed in the second radial direction opposite the first radial direction; and
the circumferential positions of two first outer prongs adjacent the particular first inner prong are aligned respectively with circumferential positions of two second outer prongs adjacent the particular second inner prong such that the at least one longitudinal channel is defined along the aligned circumferential positions of the particular first inner prong and particular second inner prong.

18. The stent assembly according to claim 1, wherein at least one fenestration for receiving a vessel is formed through the billowing graft.

19. The stent assembly according to claim 18, further comprising a radio-opaque marker placed around the at least one fenestration.

20. The stent assembly according to claim 18, wherein the at least one fenestration is formed through the billowing graft at a circumferential position corresponding to a circumferential position of a radially flat portion of the first support ring and a circumferential position of a radially flat portion of the second support ring.

21. The stent assembly according to claim 1, comprising a second graft at least partially surrounding the first graft such that the longitudinal tunnels are defined between the first graft and the second graft.

22. The stent assembly according to claim 21, wherein the billowing graft has radially depressed grooves extending longitudinally at the circumferential positions of the first inner portions of the first support ring; and the longitudinal tunnels are defined between the radially depressed channels and the second graft.

23. A prosthetic device for treatment of abdominal aortic aneurysms in a patient, comprising:
a main body formed from a plurality of circumferentially extending wires and configured for being received in an abdominal artery of the patient, the circumferentially extending wires defining one or more longitudinally extending channels and the graft covering member billowing outwardly and away from the longitudinally extending channels to contact aortic tissue along an exterior of the graft covering member when blood flows along a central fluid flow channel defined within the main body, wherein engagement of the one or more longitudinally extending channels with the graft covering member forms one or more respective, longitudinal grooves adjacent each longitudinally extending channel, wherein at least two of the one or more longitudinal grooves define an outwardly extending planar shelf along a length of the billowing graft.

24. The device according to claim 23, wherein, a longitudinally extending stent that is configured for allowing fluid flow therethrough extends within one groove of the one or more grooves.

25. The device according to claim 24, wherein the longitudinally extending stent is placed within one groove, and the longitudinally extending stent is secured within the one groove, and when blood flows along the central fluid flow channel, the graft billows to sealably engage the longitudinally extending stent.

26. The device according to claim 24, wherein one groove of the at least one groove extends beyond at least two adjacent rows of circumferentially extending wires.

27. The device according to claim 23, wherein the circumferentially extending wires forming one or more longitudinal channels are engaged with the graft member, and the graft member has a relaxed state which causes formation of the at least one groove about an inner radially facing portion of the longitudinal channels of the circumferentially extending wires.

28. The device according to claim 23, wherein at least one of the longitudinally extending grooves extends in a direction that is parallel to a direction of a central axis extending along a total length of the stent assembly.

* * * * *